US008204605B2

(12) United States Patent
Hastings et al.

(10) Patent No.: US 8,204,605 B2
(45) Date of Patent: Jun. 19, 2012

(54) MULTI-SITE ATRIAL ELECTROSTIMULATION

(75) Inventors: Roger Hastings, Maple Grove, MN (US); Daniel M. Lafontaine, Plymouth, MN (US); John A. Becker, Delano, MN (US); Michael J. Pikus, Golden Valley, MN (US); Kevin D. Edmunds, Ham Lake, MN (US); Martin R. Willard, Burnsville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 589 days.

(21) Appl. No.: 12/365,428

(22) Filed: Feb. 4, 2009

(65) Prior Publication Data

US 2009/0234407 A1    Sep. 17, 2009

Related U.S. Application Data

(60) Provisional application No. 61/063,876, filed on Feb. 7, 2008, provisional application No. 61/059,993, filed on Jun. 9, 2008.

(51) Int. Cl.
*A61N 1/05* (2006.01)

(52) U.S. Cl. .......................................... 607/119; 607/33

(58) Field of Classification Search .................. 607/4, 9, 607/30, 33, 57, 60, 116, 119
See application file for complete search history.

(56) References Cited

U.S. PATENT DOCUMENTS

| | | |
|---|---|---|
| 3,057,356 A | 10/1962 | Greatbatch |
| 3,357,434 A | 12/1967 | Abel |
| 3,596,662 A | 8/1971 | Bolduc |
| 3,667,477 A | 6/1972 | Susset et al. |
| 3,713,449 A | 1/1973 | Mulier |
| 3,727,616 A | 4/1973 | Lenzkes |
| 3,835,864 A | 9/1974 | Rasor et al. |
| 3,902,501 A | 9/1975 | Citron et al. |
| 3,942,535 A | 3/1976 | Schulman |
| 3,943,936 A | 3/1976 | Rasor et al. |
| 4,010,756 A | 3/1977 | DuMont et al. |
| 4,157,720 A | 6/1979 | Greatbatch |
| 4,162,679 A | 7/1979 | Reenstierna |

(Continued)

FOREIGN PATENT DOCUMENTS

EP    0758542 A1    2/1997

(Continued)

OTHER PUBLICATIONS

"U.S. Appl. No. 10/971,550, Notice of Allowance mailed Jul. 14, 2008", 4 pgs.

(Continued)

*Primary Examiner* — Brian T Gedeon
(74) *Attorney, Agent, or Firm* — Schwegman, Lundberg & Woessner, P.A.

(57) ABSTRACT

An apparatus and method can receive wireless energy using a wireless electrostimulation electrode assembly. In certain examples, at least some of the received wireless energy can be delivered as an electrostimulation to a heart. In certain examples, the wireless electrostimulation electrode can be mechanically supported at least partially using a ring formed by an annulus of a mitral valve of the heart. In certain examples, the wireless electrostimulation electrode assembly can be configured to be intravascularly delivered to an implant location within a chamber of the heart at the annulus of the mitral valve of the heart, and can fit entirely within the heart.

20 Claims, 14 Drawing Sheets

U.S. PATENT DOCUMENTS

| | | | |
|---|---|---|---|
| 4,198,991 A | 4/1980 | Harris |
| 4,256,115 A | 3/1981 | Bilitch |
| 4,441,210 A | 4/1984 | Hochmair et al. |
| 4,641,664 A | 2/1987 | Botvidsson |
| 4,644,957 A | 2/1987 | Ricciardelli et al. |
| 4,681,111 A | 7/1987 | Silvian |
| 4,721,118 A | 1/1988 | Harris |
| 4,830,006 A | 5/1989 | Haluska et al. |
| 4,860,750 A | 8/1989 | Frey et al. |
| 4,953,564 A | 9/1990 | Berthelsen |
| 4,987,897 A | 1/1991 | Funke |
| 5,012,806 A | 5/1991 | De Bellis |
| 5,139,033 A | 8/1992 | Everett et al. |
| 5,143,090 A | 9/1992 | Dutcher et al. |
| 5,170,802 A | 12/1992 | Mehra |
| 5,178,149 A | 1/1993 | Imburgia et al. |
| 5,193,539 A | 3/1993 | Schulman et al. |
| 5,193,540 A | 3/1993 | Schulman et al. |
| 5,234,437 A | 8/1993 | Sepetka |
| 5,250,071 A | 10/1993 | Palermo |
| 5,255,693 A | 10/1993 | Dutcher et al. |
| 5,261,916 A | 11/1993 | Engelson |
| 5,300,107 A | 4/1994 | Stokes et al. |
| 5,304,195 A | 4/1994 | Twyford, Jr. et al. |
| 5,312,415 A | 5/1994 | Palermo |
| 5,312,439 A | 5/1994 | Loeb |
| 5,314,458 A | 5/1994 | Najafi et al. |
| 5,324,316 A | 6/1994 | Schulman et al. |
| 5,324,325 A | 6/1994 | Moaddeb |
| 5,336,252 A | 8/1994 | Cohen |
| 5,342,408 A | 8/1994 | deCoriolis et al. |
| 5,350,397 A | 9/1994 | Palermo et al. |
| 5,383,915 A | 1/1995 | Adams |
| 5,383,924 A | 1/1995 | Brehier |
| 5,405,367 A | 4/1995 | Schulman et al. |
| 5,411,535 A | 5/1995 | Fujii et al. |
| 5,411,537 A | 5/1995 | Munshi et al. |
| 5,447,533 A | 9/1995 | Vachon et al. |
| 5,487,760 A * | 1/1996 | Villafana ................. 623/2.2 |
| 5,531,780 A | 7/1996 | Vachon |
| 5,571,148 A | 11/1996 | Loeb et al. |
| 5,622,168 A | 4/1997 | Keusch et al. |
| 5,735,887 A | 4/1998 | Barreras, Sr. et al. |
| 5,755,764 A | 5/1998 | Schroeppel |
| 5,772,693 A | 6/1998 | Brownlee |
| 5,779,715 A | 7/1998 | Tu |
| 5,800,535 A | 9/1998 | Howard, III |
| 5,814,089 A | 9/1998 | Stokes et al. |
| 5,833,715 A | 11/1998 | Vachon et al. |
| 5,851,227 A | 12/1998 | Spehr |
| 5,871,532 A | 2/1999 | Schroeppel |
| 5,876,429 A | 3/1999 | Schroeppel |
| 5,876,431 A | 3/1999 | Spehr et al. |
| 6,035,239 A | 3/2000 | Patag et al. |
| 6,123,724 A | 9/2000 | Denker |
| 6,132,456 A | 10/2000 | Sommer et al. |
| 6,141,588 A | 10/2000 | Cox et al. |
| 6,141,591 A | 10/2000 | Lenarz et al. |
| 6,164,284 A | 12/2000 | Schulman et al. |
| 6,200,303 B1 | 3/2001 | Verrior et al. |
| 6,208,894 B1 | 3/2001 | Schulman et al. |
| 6,223,079 B1 | 4/2001 | Bakels et al. |
| 6,240,316 B1 | 5/2001 | Richmond, Jr. et al. |
| 6,266,567 B1 | 7/2001 | Ishikawa et al. |
| 6,315,721 B2 | 11/2001 | Schulman et al. |
| 6,345,202 B2 | 2/2002 | Richmond et al. |
| 6,363,938 B2 | 4/2002 | Saadat et al. |
| 6,370,434 B1 | 4/2002 | Zhang et al. |
| 6,381,495 B1 | 4/2002 | Jenkins |
| 6,385,472 B1 | 5/2002 | Hall et al. |
| 6,409,674 B1 | 6/2002 | Brockway et al. |
| 6,445,953 B1 | 9/2002 | Bulkes et al. |
| 6,501,983 B1 * | 12/2002 | Natarajan et al. ............. 600/517 |
| 6,510,345 B1 | 1/2003 | Van et al. |
| 6,556,874 B2 | 4/2003 | Audoglio |
| 6,564,807 B1 | 5/2003 | Schulman et al. |
| 6,582,441 B1 | 6/2003 | He et al. |
| 6,589,230 B2 | 7/2003 | Gia et al. |
| 6,647,292 B1 | 11/2003 | Bardy et al. |
| 6,783,499 B2 | 8/2004 | Schwartz |
| 6,895,265 B2 | 5/2005 | Silver |
| 6,895,280 B2 | 5/2005 | Meadows et al. |
| 6,907,285 B2 * | 6/2005 | Denker et al. ................. 607/5 |
| 6,917,833 B2 | 7/2005 | Denker et al. |
| 7,003,350 B2 | 2/2006 | Denker et al. |
| 7,006,864 B2 | 2/2006 | Echt et al. |
| 7,050,849 B2 | 5/2006 | Echt et al. |
| 7,076,305 B2 | 7/2006 | Imran et al. |
| 7,184,830 B2 | 2/2007 | Echt et al. |
| 7,209,783 B2 | 4/2007 | Fellows et al. |
| 7,231,260 B2 | 6/2007 | Wallace et al. |
| 7,410,497 B2 | 8/2008 | Hastings et al. |
| 7,522,962 B1 | 4/2009 | Doron et al. |
| 7,532,932 B2 | 5/2009 | Denker et al. |
| 7,532,933 B2 | 5/2009 | Hastings et al. |
| 7,558,631 B2 | 7/2009 | Cowan et al. |
| 7,606,621 B2 | 10/2009 | Brisken et al. |
| 7,610,092 B2 | 10/2009 | Cowan et al. |
| 7,615,010 B1 | 11/2009 | Najafi et al. |
| 7,647,109 B2 | 1/2010 | Hastings et al. |
| 7,650,186 B2 | 1/2010 | Hastings et al. |
| 7,702,392 B2 | 4/2010 | Echt et al. |
| 7,765,001 B2 | 7/2010 | Echt et al. |
| 7,809,438 B2 | 10/2010 | Echt et al. |
| 7,840,281 B2 | 11/2010 | Kveen et al. |
| 7,848,815 B2 | 12/2010 | Brisken et al. |
| 7,848,823 B2 | 12/2010 | Drasler et al. |
| 7,890,173 B2 | 2/2011 | Brisken et al. |
| 7,894,904 B2 | 2/2011 | Cowan et al. |
| 7,894,907 B2 | 2/2011 | Cowan et al. |
| 7,894,910 B2 | 2/2011 | Cowan et al. |
| 7,899,541 B2 | 3/2011 | Cowan et al. |
| 7,899,542 B2 | 3/2011 | Cowan et al. |
| 7,937,161 B2 | 5/2011 | Hastings et al. |
| 7,996,087 B2 | 8/2011 | Cowan et al. |
| 8,050,774 B2 | 11/2011 | Kveen et al. |
| 2001/0018547 A1 | 8/2001 | Mechlenburg et al. |
| 2002/0026228 A1 | 2/2002 | Schauerte |
| 2002/0065543 A1 | 5/2002 | Gomperz et al. |
| 2002/0077556 A1 | 6/2002 | Schwartz |
| 2002/0123774 A1 | 9/2002 | Loeb et al. |
| 2002/0123785 A1 | 9/2002 | Zhang et al. |
| 2002/0138009 A1 | 9/2002 | Brockway et al. |
| 2002/0183791 A1 | 12/2002 | Denker et al. |
| 2002/0198604 A1 | 12/2002 | Schulman et al. |
| 2003/0036773 A1 | 2/2003 | Whitehurst et al. |
| 2003/0050681 A1 | 3/2003 | Pianca et al. |
| 2003/0074041 A1 | 4/2003 | Parry et al. |
| 2003/0088278 A1 | 5/2003 | Bardy et al. |
| 2003/0109914 A1 | 6/2003 | Westlund et al. |
| 2003/0158584 A1 | 8/2003 | Cates et al. |
| 2003/0181958 A1 | 9/2003 | Dobak |
| 2003/0181959 A1 | 9/2003 | Dobak |
| 2004/0059392 A1 | 3/2004 | Parramon et al. |
| 2004/0087831 A1 | 5/2004 | Michels et al. |
| 2004/0098068 A1 | 5/2004 | Carbunaru et al. |
| 2004/0102830 A1 | 5/2004 | Williams |
| 2004/0103906 A1 | 6/2004 | Schulman et al. |
| 2004/0106954 A1 | 6/2004 | Whitehurst et al. |
| 2004/0147973 A1 | 7/2004 | Hauser |
| 2004/0172083 A1 | 9/2004 | Penner |
| 2004/0176822 A1 | 9/2004 | Thompson et al. |
| 2005/0021108 A1 | 1/2005 | Klosterman et al. |
| 2005/0025797 A1 | 2/2005 | Wang et al. |
| 2005/0043765 A1 | 2/2005 | Williams et al. |
| 2005/0057905 A1 | 3/2005 | He et al. |
| 2005/0096702 A1 | 5/2005 | Denker et al. |
| 2005/0131511 A1 | 6/2005 | Westlund |
| 2005/0182456 A1 | 8/2005 | Ziobro et al. |
| 2005/0182465 A1 | 8/2005 | Ness |
| 2005/0251238 A1 | 11/2005 | Wallace et al. |
| 2005/0251240 A1 | 11/2005 | Doan |
| 2005/0261741 A1 | 11/2005 | Libbus et al. |
| 2005/0288727 A1 | 12/2005 | Penner |
| 2006/0015097 A1 | 1/2006 | Mulier et al. |
| 2006/0020316 A1 | 1/2006 | Martinez et al. |
| 2006/0085039 A1 | 4/2006 | Hastings et al. |

| | | | |
|---|---|---|---|
| 2006/0085041 A1 | 4/2006 | Hastings et al. | |
| 2006/0085042 A1 | 4/2006 | Hastings et al. | |
| 2006/0095089 A1 | 5/2006 | Soykan et al. | |
| 2006/0136001 A1 | 6/2006 | Ortega et al. | |
| 2006/0136004 A1 | 6/2006 | Cowan et al. | |
| 2006/0173504 A1* | 8/2006 | Zhu et al. | 607/9 |
| 2006/0173505 A1* | 8/2006 | Salo et al. | 607/9 |
| 2006/0178719 A1 | 8/2006 | Ideker et al. | |
| 2006/0206170 A1 | 9/2006 | Denker et al. | |
| 2007/0075905 A1 | 4/2007 | Denker et al. | |
| 2007/0106357 A1* | 5/2007 | Denker et al. | 607/116 |
| 2007/0135882 A1 | 6/2007 | Drasler et al. | |
| 2007/0135883 A1 | 6/2007 | Drasler et al. | |
| 2007/0150009 A1 | 6/2007 | Kveen et al. | |
| 2007/0150037 A1 | 6/2007 | Hastings et al. | |
| 2007/0150038 A1 | 6/2007 | Hastings et al. | |
| 2007/0203556 A1 | 8/2007 | Rutten et al. | |
| 2007/0219590 A1 | 9/2007 | Hastings et al. | |
| 2007/0239248 A1 | 10/2007 | Hastings et al. | |
| 2008/0021505 A1 | 1/2008 | Hastings et al. | |
| 2008/0021532 A1 | 1/2008 | Kveen et al. | |
| 2008/0039904 A1 | 2/2008 | Bulkes et al. | |
| 2008/0046040 A1 | 2/2008 | Denker et al. | |
| 2008/0077184 A1 | 3/2008 | Denker et al. | |
| 2008/0077188 A1 | 3/2008 | Denker et al. | |
| 2008/0109054 A1 | 5/2008 | Hastings et al. | |
| 2008/0319502 A1 | 12/2008 | Sunagawa et al. | |
| 2009/0018599 A1 | 1/2009 | Hastings et al. | |
| 2009/0204170 A1 | 8/2009 | Hastings et al. | |
| 2010/0100144 A1 | 4/2010 | Shuros et al. | |
| 2010/0314775 A1 | 12/2010 | Schwarzbauer | |
| 2011/0034939 A1 | 2/2011 | Kveen et al. | |
| 2011/0213233 A1 | 9/2011 | Stevenson et al. | |

FOREIGN PATENT DOCUMENTS

| | | |
|---|---|---|
| EP | 1166820 A2 | 1/2002 |
| EP | 1166832 A1 | 1/2002 |
| EP | 1809372 A1 | 7/2007 |
| EP | 1812104 A1 | 8/2007 |
| EP | 1835962 A1 | 9/2007 |
| FR | 2559391 | 8/1985 |
| JP | 62-254770 A | 6/1987 |
| JP | 02307481 A | 12/1990 |
| JP | 5-76501 A2 | 3/1993 |
| JP | 5245215 | 9/1993 |
| JP | 2005245215 A | 9/1993 |
| JP | 6510459 A | 11/1994 |
| JP | 7016299 A | 1/1995 |
| JP | 9508054 A | 8/1997 |
| JP | 10-509901 | 9/1998 |
| JP | 2000-502931 A | 3/2000 |
| JP | 2002510222 A | 4/2002 |
| JP | 2002-514478 A | 5/2002 |
| JP | 2004-173790 A | 6/2004 |
| JP | 2010509901 | 3/2010 |
| NZ | 526115 | 10/2006 |
| NZ | 539770 | 10/2007 |
| NZ | 539771 | 10/2007 |
| WO | WO-95/10226 A1 | 4/1995 |
| WO | WO-9620754 A1 | 7/1996 |
| WO | WO-9725098 A1 | 7/1997 |
| WO | WO-98/26840 A1 | 6/1998 |
| WO | WO-99/06102 A1 | 2/1999 |
| WO | WO-9958191 A1 | 11/1999 |
| WO | WO-99/64104 A1 | 12/1999 |
| WO | WO-00/30534 A1 | 6/2000 |
| WO | WO-01/00114 A1 | 1/2001 |
| WO | WO-03/053491 A2 | 7/2003 |
| WO | WO-03/076010 A1 | 9/2003 |
| WO | WO-2004/002572 A1 | 1/2004 |
| WO | WO-2004012811 A1 | 2/2004 |
| WO | WO-2005/101660 A1 | 10/2005 |
| WO | WO-2006/045073 A1 | 4/2006 |
| WO | WO-2006/045074 A2 | 4/2006 |
| WO | WO-2006/045075 A1 | 4/2006 |
| WO | WO-2006/096685 A1 | 9/2006 |
| WO | WO-2007/067231 A1 | 6/2007 |
| WO | WO-2007/067253 A1 | 6/2007 |
| WO | WO-2007/078770 A2 | 7/2007 |
| WO | WO-2007/115044 A2 | 10/2007 |
| WO | WO-2008/011626 A1 | 1/2008 |
| WO | WO-2008/034005 A2 | 3/2008 |
| WO | WO-2008/111998 A1 | 9/2008 |
| WO | WO-2009/099597 A1 | 8/2009 |

OTHER PUBLICATIONS

"U.S. Appl. No. 10/971,550, Notice of Allowance mailed Dec. 22, 2008", 4 pgs.

"U.S. Appl. No. 10/971,550, Non- Final Office Action mailed Mar. 19, 2007", 11 pgs.

"U.S. Appl. No. 10/971,550, Non-Final Office Action mailed Nov. 5, 2007", 19 pgs.

"U.S. Appl. No. 10/971,550, Response Filed Sep. 4, 2007 to Non-Final Office Action mailed Mar. 19, 2007", 15 pgs.

"U.S. Appl. No. 10/971,550, Response filed Mar. 25, 2008 to Non Final Office Action mailed Nov. 5, 2007", 17 pgs.

"U.S. Appl. No. 10/971,550, Amendment Under 37 C.F.R. Sec. 1.312 filed Mar. 20, 2009", 6 pgs.

"U.S. Appl. No. 11/075,375, Response filed May 22, 2008 to Final Office Action mailed Jan. 23, 2008", 16 pgs.

"U.S. Appl. No. 11/075,375, Non-Final Office Action mailed Jun. 8, 2007", 11 pgs.

"U.S. Appl. No. 11/075,375, Response filed Oct. 26, 2007 to Non-Final Office Action mailed Jun. 8, 2007", 10 pgs.

"U.S. Appl. No. 11/075,375, Final Office Action mailed Jan. 23, 2008", 10 pgs.

"U.S. Appl. No. 11/075,375 ,Final Office Action mailed Apr. 16, 2009", 10 pgs.

"U.S. Appl. No. 11/075,375, Amendment and Response filed Jan. 12, 2009 to Non-Final Office Action mailed Aug. 11, 2008", 18 pgs.

"U.S. Appl. No. 11/075,375, Non-Final Office Action mailed Aug. 11, 2008", 15 pgs.

"U.S. Appl. No. 11/075,375, Response filed Jul. 16, 2009 to Final Office Action mailed Apr. 16, 2009", 13 pgs.

"U.S. Appl. No. 11/075,376, Response filed Jun. 9, 2008 to Final Office Action mailed Jan. 7, 2008", 20 pgs.

"U.S. Appl. No. 11/075,376, Non-Final Office Action Mailed Aug. 20, 2008", 15 pgs.

"U.S. Appl. No. 11/075,376, Final Office Action mailed Jan. 7, 2008", 11 pgs.

"U.S. Appl. No. 11/075,376, Non-Final Office Action mailed Jun. 26, 2007", 9 pgs.

"U.S. Appl. No. 11/075,376, Response filed Jan. 21, 2009 to Non-Final Office Action mailed Aug. 20, 2008", 22 pgs.

"U.S. Appl. No. 11/075,376, Response filed Oct. 26, 2007 to Non-Final Office Action mailed Jun. 26, 2007", 14 pgs.

"U.S. Appl. No. 11/075,376, Final Office Action mailed Apr. 8, 2009", 17 pgs.

"U.S. Appl. No. 11/075,376, Notice of Allowance mailed Aug. 24, 2009", 6 pgs.

"U.S. Appl. No. 11/075,376, Response filed Jul. 8, 2009 to Final Office Action mailed Apr. 8, 2009", 11 pgs.

"U.S. Appl. No. 11/394,601, Non-Final Office Action mailed Sep. 2, 2009", 6 pgs.

"U.S. Appl. No. 11/490,916, Response filed Sep. 3, 2009 to Non Final Office Action mailed May 5, 2009", 13 pgs.

"U.S. Appl. No. 11/511,152, Final Office Action mailed Aug. 10, 2009", 13 pgs.

"U.S. Appl. No. 11/549,352, Non-Final Office Action mailed Feb. 5, 2008", 11 pgs.

"U.S. Appl. No. 11/549,352, Final Office Action mailed Mar. 9, 2009", 10 pgs.

"U.S. Appl. No. 11/549,352, Notice of Panel Decision from Pre-Appeal Brief Review mailed Feb. 2, 2009", 2 pgs.

"U.S. Appl. No. 11/549,352, Pre-Appeal Brief for Review filed Dec. 20, 2008", 5 pgs.

"U.S. Appl. No. 11/549,352, Response filed Jul. 7, 2008 to Non-Final Office Action mailed Feb. 5, 2008", 17 pgs.

"U.S. Appl. No. 11/683,577, Non-Final Office Action mailed Mar. 5, 2009", 13 pgs.

"U.S. Appl. No. 11/683,577, Response filed Aug. 5, 2009 to Non Final Office Action mailed Mar. 5, 2009", 10 pgs.
"U.S. Appl. No. 11/683,584, Non-Final Office Action mailed Apr. 1, 2009", 9 pgs.
"U.S. Appl. No. 11/683,584, Response filed Jul. 1, 2009 to Non Final Office Action mailed Apr. 1, 2009", 7 pgs.
"U.S. Appl. No. 11/745,070, Non Final Office Action mailed Apr. 27, 2009", 11 pgs.
"U.S. Appl. No. 11/745,070, Response filed Jul. 27, 2009 to Non Final Office Action mailed Apr. 27, 2009", 11 pgs.
"U.S. Appl. No. 11/549,352, Final Office Action mailed on Aug. 26, 2008", 13 pgs.
"U.S. Appl. No. 11/549,352, Appeal Brief filed Sep. 9, 2009", 37 pgs.
"European Application Serial No. 06790023.3, Office Action mailed Mar. 4, 2009", 6 pgs.
"European Application Serial No. 06825988.6, Office Action mailed Mar. 4, 2009", 7 pgs.
"European Application Serial No. 07759589.0, Office Action mailed Jan. 29, 2009", 3 pgs.
"European Application Serial No. 07759589.0, Response filed Jun. 5, 2009 to Office Action mailed Jan. 29, 2009", 6 pgs.
"International Application Serial No. PCT/US2006/040291, International Search Report mailed Apr. 4, 2007", 5 pgs.
"International Application Serial No. PCT/US2006/040291, Written Opinion mailed Apr. 4, 2007", 9 pgs.
"International Application Serial No. PCT/US2005/037978, International Search Report mailed Jun. 13, 2006", 5 pgs.
"International Application Serial No. PCT/US2005/037978, Written Opinion mailed Jun. 13, 2006", 12 pgs.
"International Application Serial No. PCT/US2005/037979, International Search Report mailed Mar. 21, 2006", 4 pgs.
"International Application Serial No. PCT/US2005/037979, Written Opinion mailed Mar. 21, 2006", 8 pgs.
"International Application Serial No. PCT/US2007/078405, International Search Report mailed May 20, 2008", 5 pgs.
"International Application Serial No. PCT/US2007/078405, Written Opinion mailed May 20, 2008", 7 pgs.
"International Application Serial No. PCT/US2009/000587, International Search Report mailed Apr. 24, 2009", 4 pgs.
"International Application Serial No. PCT/US2009/000587 Written Opinion mailed Apr. 24, 2009", 8.pgs.
"International Application Serial No. PCT/US2009/000693, International Search Report mailed May 8, 2009", 5 pgs.
"International Application Serial No. PCT/US2009/000693, Written Opinion mailed May 8, 2009", 8 pgs.
"Telemetry Research Transcutaneous Energy Transfer (TET) Technology Summary", *Telemetry Research Ltd.*, www.telemetryresearch.com, (No date listed), 1 pg.
Busch, M., et al., "On the Heating of Inductively Coupled Resonators (Stents) During MRI Examinations", *Magnetic Resonance in Medicine*, 54, (2005), 775-785.
Manoharan, G., et al., "Novel passive implantable atrial defibrillator using transcutaneous radiofrequency energy transmission successfully cardioverts atrial fibrillation.", *Circulation*, 108(11), (Sep. 16, 2003), 1382-1388.
Piella, J. P., "Energy management, wireless and system solutions for highly integrated implantable devices", *Doctoral Thesis by Jordi Parramon I Piella for the Universitat Autonoma de Barcelona, certified Dec. 2001*, (2001), 62 pgs.
Si, P., et al., "A Frequency Control Method for Regulating Wireless Power to Implantable Devices", *IEEE Transactions on Biomedical Circuits and Systems*, 2(1), (Mar. 2008), 22-29.
Swain, E., "Breakthrough Products Could Put Lesser-Known Firms on the map", *MDDI*, (Apr. 2004), 6 pgs.
Wagner, B. K, "Electrodes, Leads, and Biocompatibility", *Chapter 6—Design of Cardiac Pacemakers*, edited by John G. Webster., (1995), 133-160.
U.S. Appl. No. 11/394,601, Response filed Dec. 2, 2009 to Non Final Office Action mailed Sep. 2, 2009, 11 pgs.
U.S. Appl. No. 11/511,152, Response filed Nov. 12, 2009 to Final Office Action mailed Aug. 10, 2009, 13 pgs.
U.S. Appl. No. 11/683,577, Final Office Action mailed Nov. 9, 2009, 14 pgs.
U.S. Appl. No. 11/745,105, Non Final Office Action mailed Sep. 18, 2009, 9 pgs.
"U.S. Appl. No. 10/971,550, Examiner Interview Summary mailed Jan. 22, 2008", 4 pgs.
"U.S. Appl. No. 10/971,550, Response to 312 Amendment mailed Apr. 6, 2009", 2 pgs.
"U.S. Appl. No. 11/075,375, Examiner Interview Summary mailed Jan. 12, 2009", 4 pgs.
"U.S. Appl. No. 11/075,375, Examiner Interview Summary mailed May 1, 2008", 4 pgs.
"U.S. Appl. No. 11/075,375, Notice of Allowance mailed Sep. 4, 2009", 6 pgs.
"U.S. Appl. No. 11/075,376, Examiner Interview Summary mailed Jan. 12, 2009", 4 pgs.
"U.S. Appl. No. 11/075,376, Examiner Interview Summary mailed Apr. 2, 2008", 4 pgs.
"U.S. Appl. No. 11/316,120, Decision on Pre-Appeal Brief mailed Apr. 19, 2011", 2 pgs.
"U.S. Appl. No. 11/316,120, Final Office Action mailed Oct. 28, 2010", 8 pgs.
"U.S. Appl. No. 11/316,120, Non-Final Office Action mailed Apr. 11, 2008", 7 pgs.
"U.S. Appl. No. 11/316,120, Non-Final Office Action mailed May 27, 2010", 7 pgs.
"U.S. Appl. No. 11/316,120, Notice of Allowance mailed Jul. 20, 2011", 7 pgs.
"U.S. Appl. No. 11/316,120, Pre-Appeal Brief Request filed Mar. 25, 2011", 5 pgs.
"U.S. Appl. No. 11/316,120, Response filed Mar. 25, 2011 to Final Office Action mailed Oct. 28, 2010", 8 pgs.
"U.S. Appl. No. 11/316,120, Response filed Apr. 12, 2010 to Final Office Action mailed Nov. 12, 2009", 12 pgs.
"U.S. Appl. No. 11/316,120, Response filed May 14, 2008 to Non-Final Office Action mailed Apr. 11, 2008", 12 pgs.
"U.S. Appl. No. 11/316,120, Response filed Aug. 27, 2010 to Non-Final Office Action mailed May 27, 2010", 13 pgs.
"U.S. Appl. No. 11/316,120, Supplemental Notice of Allowance mailed Sep. 1, 2011", 4 pgs.
"U.S. Appl. No. 11/394,601, Decision on Pre-Appeal Brief mailed Oct. 6, 2010", 2 pgs.
"U.S. Appl. No. 11/394,601, Final Office Action mailed Mar. 22, 2010", 7 pgs.
"U.S. Appl. No. 11/394,601, Notice of Allowance mailed Dec. 28, 2010", 8 pgs.
"U.S. Appl. No. 11/394,601, Pre-Appeal Brief Request filed Jul. 21, 2010", 5 pgs.
"U.S. Appl. No. 11/490,576, Decision on Pre-Appeal Brief mailed Aug. 30, 2011", 2 pgs.
"U.S. Appl. No. 11/490,576, Final Office Action mailed Jan. 19, 2011", 12 pgs.
"U.S. Appl. No. 11/490,576, Non-Final Office Action mailed Nov. 9, 2011", 9 pgs.
"U.S. Appl. No. 11/490,576, Non-Final Office Action mailed Jul. 12, 2010", 8 pgs.
"U.S. Appl. No. 11/490,576, Pre-Appeal Brief Request filed May 12, 2011", 5 pgs.
"U.S. Appl. No. 11/490,576, Response filed Mar. 5, 2010 to Non-Final Office Action mailed Oct. 5, 2009", 13 pgs.
"U.S. Appl. No. 11/490,576, Response filed Oct. 4, 2010 to Non-Final Office Action mailed Jul. 12, 2010", 15 pgs.
"U.S. Appl. No. 11/490,916, Examiner Interview Summary mailed Apr. 12, 2010", 3 pgs.
"U.S. Appl. No. 11/490,916, Examiner Interview Summary mailed Aug. 19, 2009", 2 pgs.
"U.S. Appl. No. 11/490,916, Final Office Action mailed Dec. 17, 2009", 11 pgs.
"U.S. Appl. No. 11/490,916, Notice of Allowance mailed Jul. 9, 2010", 4 pgs.
"U.S. Appl. No. 11/490,916, Response filed Jan. 12, 2009 to Restriction Requirement Dec. 11, 2008", 7 pgs.
"U.S. Appl. No. 11/490,916, Response filed Apr. 15, 2010 to Final Office Action mailed Dec. 17, 2009", 12 pgs.

"U.S. Appl. No. 11/490,916, Supplemental Notice of Allowability mailed Oct. 14, 2010", 2 pgs.
"U.S. Appl. No. 11/511,152, Non-Final Office Action mailed Dec. 30, 2009", 13 pgs.
"U.S. Appl. No. 11/511,152, Notice of Allowance mailed Jul. 28, 2010", 6 pgs.
"U.S. Appl. No. 11/511,152, Preliminary Amendment filed Oct. 17, 2006", 3 pgs.
"U.S. Appl. No. 11/511,152, Response filed Jun. 30, 2010 to Non-Final Office Action mailed Dec. 30, 2009", 12 pgs.
"U.S. Appl. No. 11/549,352, Examiner Interview Summary mailed Jun. 25, 2008", 2 pgs.
"U.S. Appl. No. 11/549,352, Examiner's Answer mailed Nov. 27, 2009 to Appeal Brief filed Sep. 9, 2009", 12 pgs.
"U.S. Appl. No. 11/549,352, Reply Brief filed Jan. 27, 2010", 8 pgs.
"U.S. Appl. No. 11/683,577, Examiner Interview Summary mailed Jul. 7, 2009", 4 pgs.
"U.S. Appl. No. 11/683,577, Response filed May 7, 2010 to Final Office Action mailed Nov. 9, 2009", 14 pgs.
"U.S. Appl. No. 11/683,584, Examiner Interview Summary mailed Jul. 7, 2009", 4 pgs.
"U.S. Appl. No. 11/683,584, Final Office Action mailed Jan. 29, 2010", 9 pgs.
"U.S. Appl. No. 11/683,584, Preliminary Amendment filed Mar. 8, 2007", 1 pg.
"U.S. Appl. No. 11/683,584, Response filed Jul. 21, 2010 to Final Office Action mailed Jan. 29, 2010", 12 pgs.
"U.S. Appl. No. 11/745,070, Final Office Action mailed Dec. 11, 2009", 18 pgs.
"U.S. Appl. No. 11/745,105, Final Office Action mailed Mar. 30, 2010", 9 pgs.
"U.S. Appl. No. 11/745,105, Non-Final Office Action mailed May 11, 2011", 13 pgs.
"U.S. Appl. No. 11/745,105, Notice of Allowance mailed Oct. 31, 2011", 5 pgs.
"U.S. Appl. No. 11/745,105, Response filed Jan 19, 2010 to Non-Final Office Action mailed Sep. 18, 2009", 12 pgs.
"U.S. Appl. No. 11/745,105, Response filed Jun. 22, 2009 to Restriction Requirement mailed May 21, 2009", 6 pgs.
"U.S. Appl. No. 11/745,105, Response filed Jul. 29, 2010 to Final Office Action mailed Mar. 30, 2010", 12 pgs.
"U.S. Appl. No. 11/745,105, Response filed Sep. 12, 2011 to Non-Final Office Action mailed May 11, 2011", 13 pgs.
"U.S. Appl. No. 11/745,105, Restriction Requirement mailed May 21, 2009", 6 pgs.
"U.S. Appl. No. 12/361,884, Non-Final Office Action mailed Oct. 12, 2011", 16 pgs.
"U.S. Appl. No. 12/361,884, Preliminary Amendment filed Jun. 30, 2011", 12 pgs.
"U.S. Appl. No. 12/361,884, Supplemental Preliminary Amendment filed Jul. 27, 2011", 12 pgs.
"U.S. Appl. No. 12/910,106, Non Final Office Action mailed Apr. 4, 2011", 9 pgs.
"U.S. Appl. No. 12/910,106, Notice of Allowance mailed Jan. 26, 2012", 6 pgs.
"U.S. Appl. No. 12/910,106, Notice of Allowance mailed Oct. 27, 2011", 5 pgs.
"U.S. Appl. No. 12/910,106, Response filed Aug. 2, 2011 to Non-Final Office Action mailed Apr. 4, 2011", 14 pgs.
"European Application Serial No. 05815206.7, Communication Dec. 18, 2009", 4 pgs.
"European Application Serial No. 05815206.7, Response filed Apr. 19, 2010 to Communication Dec. 18, 2009", 27 pgs.
"European Application Serial No. 05817448.3, Communication mailed Dec. 18, 2009", 2 pgs.
"European Application Serial No. 05817448.3, Response filed Mar. 19, 2010 to Communication mailed Dec. 18, 2009", 9 pgs.
"European Application Serial No. 07759589.0, Office Action Mailed Feb. 18, 2010", 3 pgs.
"European Application Serial No. 07759589.0, Response filed Jun. 24, 2010 to Office Action mailed Feb. 18, 2010", 6 pgs.
"European Application Serial No. 07759589.0, Summons to Attend Oral Proceedings mailed May 17, 2011", 3 pgs.
"European Application Serial No. 07759589.0, Written Submission filed Dec. 5, 2011 to Summons to Attend Oral Proceedings dated May 17, 2011", 16 pgs.
"Japanese Application Serial No. 2007-538087, Office Action mailed Apr. 11, 2011", (w/ English Translation), 5 pgs.
"Japanese Application Serial No. 2007-538087, Office Action mailed Oct. 5, 2011", (w/ English Translation), 14 pgs.
"Japanese Application Serial No. 2007-538087, Response filed Jun. 27, 2011 to Office Action dated Apr. 11, 2011", (w/ English Translation of Amended Claims), 12 pgs.
"Japanese Application Serial No. 2007-538088, Notice of Final Rejection mailed Dec. 6, 2011", (w/ English Translation), 9 pgs.
"Japanese Application Serial No. 2007-538088, Office Action mailed Jun. 13, 2011", (w/ English Translation), 5 pgs.
"Japanese Application Serial No. 2007-538088, Response filed Aug. 25, 2011 to Office Action dated Jun. 13, 2011", (w/ English Translation of Amended Claims), 9 pgs.
"Japanese Application Serial No. 2008-544324, Office Action mailed Nov. 22, 2011", (w/ English Translation), 5 pgs.
"Japanese Application Serial No. 2008-544332, Office Action mailed Nov. 29, 2011", (w/ English Translation), 5 pgs.

* cited by examiner

MULTI-SITE ATRIAL ELECTROSTIMULATION

CROSS REFERENCE TO RELATED APPLICATIONS

This patent application claims the benefit of priority, under 35 U.S.C. Section 119(e), to Roger Hastings et al., U.S. Provisional Patent Application Ser. No. 61/063,876, entitled "WIRELESS STENT ELECTROSTIMULATION SYSTEM," filed on Feb. 7, 2008, incorporated herein by reference in its entirety.

This patent application also claims the benefit of priority, under 35 U.S.C. Section 119(e), to Roger Hastings et al., U.S. Provisional Patent Application Ser. No. 61/059,993, entitled "WIRELESS TISSUE ELECTROSTIMULATION SYSTEM," filed on Jun. 9, 2008, incorporated herein by reference in its entirety.

BACKGROUND

Electrostimulation can be used to treat acute and chronic patient conditions, such as to elicit or inhibit heart muscle contractions, for example, using a cardiac rhythm management device. Cardiac rhythm management devices can include, for example, implantable pacemakers, implantable cardiac re-synchronization therapy devices, and implantable cardioverter defibrillators, among others. Cardiac rhythm management devices can be used to treat conditions such as atrial or ventricular tachycardia, atrial or ventricular fibrillation, bradycardia, and congestive heart failure, among other diseases.

An example of a cardiac rhythm management device can include a battery-operated electronics unit implanted under the skin, such as in the pectoral region, connected to one or more implantable flexible intravascular leads implanted using a catheter-based delivery system, such as to reach a location within a heart chamber or one or more coronary blood vessels.

Such leads can include one or more exposed electrodes to directly electrostimulate cardiac tissue, or to sense potentials at the tissue (e.g., for sensing intrinsic cardiac activity, or sensing an evoked response to the application of electrostimulus). Tissue growth can encapsulate the electrode. This can reduce a required electrostimulus threshold energy to achieve a desired response, but can also present a challenge if lead re-positioning or removal is needed. This may preclude using multiple leads in certain locations. Epicardial electrostimulus locations can also be used, such as when acute pacing therapy is desired and pericardial cavity access is available.

OVERVIEW

Some conditions, such as supraventricular tachyarrhythmias (SVTs), can benefit from atrial electrostimulation (e.g., pacing, or one or more other forms of electrical stimulation) at one or more sites within or near a left or right atrium of a heart, or both. In certain examples, electrostimulation can be used to depolarize tissue near one or more wireless electrostimulation electrode assemblies (e.g., including one or more electrodes that are not "tethered" by an intravascular leadwire to a CRM device electronics unit), such as to disrupt a "circus" depolarization wavefront, such as to terminate a tachyarrhythmia. In certain examples, electrostimulation can be used to spatially coordinate or resynchronize contractions within or between the left and right atria. In certain examples, this can help improve atrial hemodynamics or reduce the risk of stroke, such as due to a blood clot (e.g., a thrombus) forming in stagnant blood in one or more heart chambers.

Example 1 describes an apparatus. In this example, the apparatus can include a first wireless electrostimulation electrode assembly including an electrostimulation circuit, a wireless receiver configured to receive wireless energy and configured to provide at least some of the received wireless energy to the electrostimulation circuit, a first expandable support mechanically coupled to the electrostimulation circuit and the wireless receiver and configured to conform to, and at least partially encircle, a ring formed by an annulus of a mitral valve of a heart. In this example, the electrostimulation circuit can be configured to deliver at least some of the received wireless energy as an electrostimulation to the heart, the first wireless electrostimulation electrode assembly can be configured to be intravascularly delivered to an implant location within a chamber of the heart at the annulus of the mitral valve of the heart, and the first wireless electrostimulation electrode assembly can be configured to fit entirely within the heart.

In Example 2, the wireless energy of Example 1 optionally includes magnetically-coupled energy, and the wireless receiver can be optionally configured to receive the magnetically-coupled energy.

In Example 3, the apparatus of any one or more of Examples 1-2 optionally includes a transmitter configured to provide the magnetically-coupled energy, and the transmitter is optionally sized and shaped to be located subcutaneously within a patient, or outside a patient body.

In Example 4, the electrostimulation circuit of any one or more of Examples 1-3 can be optionally configured to deliver an electrostimulation including enough of the received wireless energy to depolarize cardiac tissue near the wireless electrostimulation electrode assembly.

In Example 5, the first expandable support of any one or more of Examples 1-4 optionally includes a shape memory material configured to provide an expansion force, and the first expandable support can be optionally configured to anchor the first wireless electrostimulation electrode assembly at the implant location at the annulus of the mitral valve at least in part using the expansion force when the first wireless electrostimulation electrode assembly is delivered to the implant location.

In Example 6, the first wireless electrostimulation electrode assembly of any one or more of Examples 1-5 optionally includes one or more extending tines configured to controllably extend into tissue when the first wireless electrostimulation electrode assembly is delivered to the implant location at the annulus of the mitral valve of the heart.

In Example 7, the apparatus of any one or more of Examples 1-6 optionally includes a second wireless electrostimulation electrode assembly configured to be intravascularly delivered to an implant location within a blood vessel and configured to provide an electrostimulation to the heart near the blood vessel, and a controller communicatively coupled to the first and second wireless electrostimulation electrode assemblies, the controller optionally configured to coordinate delivery of the electrostimulation by the first and second wireless electrostimulation electrode assemblies.

In Example 8, the blood vessel of any one or more of Examples 1-7 can be optionally selected from a list including a pulmonary vein, a coronary sinus, or a vena cava.

In Example 9, the apparatus of any one or more of Examples 1-8 optionally includes a second electrostimulation electrode assembly configured to be intravascularly delivered to an endocardial location at an atrial appendage of the heart and configured to provide an electrostimulation to the heart, and a controller communicatively coupled to the first and second wireless electrostimulation electrode assemblies, the controller optionally configured to coordinate delivery of the electrostimulation by the first and second wireless electrostimulation electrode assemblies.

In Example 10, the atrial appendage of the heart of any one or more of Examples 1-9 can optionally be a left atrial appendage, the second electrostimulation electrode assembly optionally includes a second expandable support configured to at least partially block the opening to the left atrial appendage of the heart, and the second expandable support can be optionally configured to anchor the second electrostimulation electrode assembly at the opening of the left atrial appendage when the second expandable support is expanded.

In Example 11, the apparatus of any one or more of Examples 1-10 optionally includes a plurality of separate wireless electrostimulation electrode assemblies, each optionally configured to be intravascularly delivered to a respective implant location and each configured to provide an electrostimulation to the heart at the respective implant location, a controller communicatively coupled to the plurality of separate wireless electrostimulation electrode assemblies, the controller optionally configured to coordinate delivery of the electrostimulation to the heart at each respective implant location, and the plurality of separate wireless electrostimulation electrode assemblies optionally including the first wireless electrostimulation electrode assembly.

In Example 12, the plurality of separate wireless electrostimulation electrode assemblies of any one or more of Examples 1-11 optionally includes one or more wireless electrostimulation electrode assemblies selected from a list including a second wireless electrostimulation electrode assembly configured to be intravascularly delivered to an endocardial location at an atrial septum of the heart and configured to provide an electrostimulation to the heart, a third wireless electrostimulation electrode assembly configured to be intravascularly delivered to an endocardial location at an atrial appendage of the heart and configured to provide an electrostimulation to the heart, a fourth wireless electrostimulation electrode assembly configured to be intravascularly delivered to an implant location within a pulmonary vein and configured to provide an electrostimulation to the heart, a fifth wireless electrostimulation electrode assembly configured to be intravascularly delivered to an implant location within a vena cava and configured to provide an electrostimulation to the heart, a sixth wireless electrostimulation electrode assembly configured to be intravascularly delivered to an implant location within a coronary sinus and configured to provide an electrostimulation the heart. In this example, the controller can be communicatively coupled to each corresponding wireless electrostimulation electrode assembly and the controller can be optionally configured to coordinate delivery of the electrostimulation to the heart at each respective implant location by each respective wireless electrostimulation electrode assembly.

In Example 13, the controller of any one or more of Examples 1-12 optionally includes an arrhythmia detector configured to detect an arrhythmia, and the controller can be optionally configured to coordinate delivery of the electrostimulation to the heart at each respective implant location to terminate the arrhythmia in response to information provided by the arrhythmia detector.

In Example 14, the arrhythmia of any one or more of Examples 1-13 can optionally include an atrial tachyarrhythmia selected from a list including an atrial fibrillation, an atrial tachycardia, an atrial flutter, an atrioventricular nodal reentrant tachycardia, or an atrioventricular reentrant tachycardia.

In Example 15, the controller of any one or more of Examples 1-14 can be optionally configured to coordinate delivery of the electrostimulation to the heart at each respective implant location to terminate the arrhythmia without exceeding a pain threshold of a patient.

Example 16 describes a method. In this example, the method includes receiving wireless energy using a first wireless electrostimulation electrode assembly, delivering at least some of the received wireless energy as an electrostimulation to a heart, mechanically supporting the first wireless electrostimulation electrode assembly at least partially using a ring formed by an annulus of a mitral valve of the heart, wherein the first wireless electrostimulation electrode assembly can be configured to be intravascularly delivered to an implant location within a chamber of the heart at the annulus of the mitral valve of the heart, and the first wireless electrostimulation electrode assembly can be configured to fit entirely within the heart.

In Example 17, the method of Example 16 optionally includes receiving wireless energy using a plurality of separate wireless electrostimulation electrode assemblies, the plurality optionally including the first wireless electrostimulation electrode assembly, and the plurality of separate wireless electrostimulation electrode assemblies can each be optionally configured to be intravascularly delivered to a respective implant location, delivering one or more coordinated electrostimulations to the heart at the respective implant location using at least one of the plurality of electrostimulation electrode assemblies and using at least some of the received wireless energy.

In Example 18, the method of any one or more of Examples 16-17 optionally includes detecting an arrhythmia, terminating the detected arrhythmia using the delivering one or more coordinated electrostimulations and using information provided by the detecting the arrhythmia, the delivering one or more coordinated electrostimulations optionally includes delivering enough received wireless energy to depolarize cardiac tissue at each respective implant location where the one or more coordinate electrostimulations are delivered.

In Example 19, the detecting the arrhythmia of any one or more of Examples 16-18 optionally includes detecting an atrial arrhythmia selected from a list including an atrial fibrillation, an atrial tachycardia, an atrial flutter, an atrioventricular nodal reentrant tachycardia, or an atrioventricular reentrant tachycardia.

In Example 20, the terminating the arrhythmia using the delivering the one or more coordinated electrostimulations of any one or more of Examples 16-19 optionally includes depolarizing enough cardiac tissue to terminate the arrhythmia without exceeding a pain threshold of a patient.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
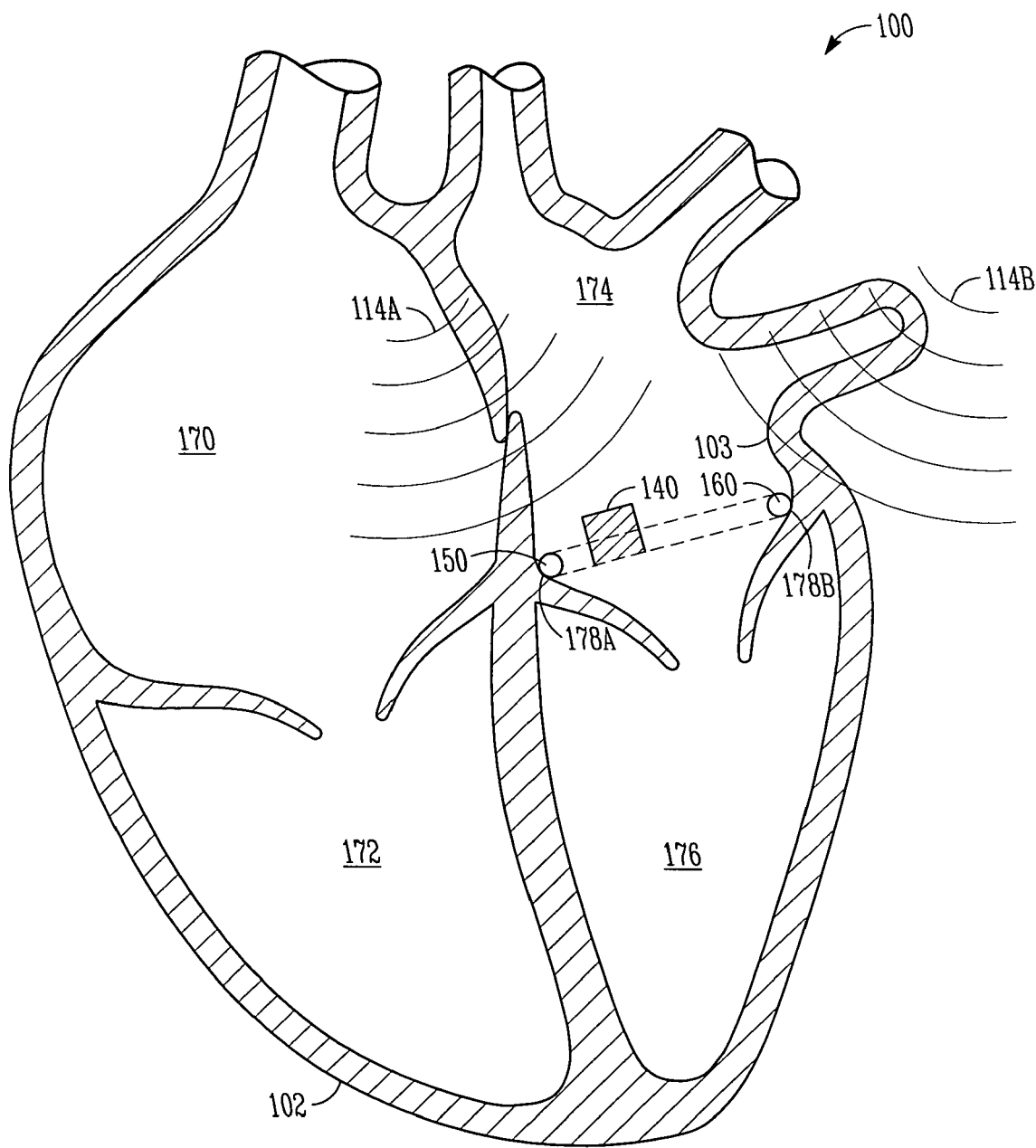
FIG. 1 illustrates generally an example of an apparatus including a wireless electrostimulation electrode assembly at a mitral valve annulus location.

Atrial tachyarrhythmias can be uni-focal, multi-focal, or unfocused. They can originate in a left or right atrium, or elsewhere, involving one or more conduction pathways through atrial heart tissue. A uni-focal atrial tachyarrhythmia can involve an ectopic focus in the atrium, and can result in a "circus" depolarization wavefront, such as within one or both atria. A multifocal atrial tachyarrhythmia can involve multiple ectopic foci in one or both atria, and can result in multiple "circus" wavefronts. In certain examples, coordinated electrostimulation can be delivered to multiple atrial wireless electrostimulation electrode implant locations, such as to depolarize cardiac tissue to disrupt the one or more "circus" wavefronts to terminate the arrhythmia, whether uni-focal or multi-focal. Similarly, in certain examples, atrioventricular tachyarrhythmias such as AV nodal reentrant tachycardia (AVNRT), atrioventricular reentrant tachycardia (AVRT), or atrial flutter, may be terminated or regulated (e.g., controlled by high-rate pacing, or one or more other electrostimulations). This can involve disrupting one or more primary or accessory conduction pathways followed by one or more arrhythmic depolarization waves, such as by using one or more wireless electrostimulation electrode assemblies to provide coordinated electrostimulations nearby. The likelihood of disrupting a pathway used by a reentrant depolarization (and thus terminating the arrhythmia) can increase as the energy used for electrostimulation increases or as the number of electrostimulation sites increases. Thus, the present inventors have recognized, among other things, that providing at least one electrostimulation electrode assembly in the left atrium (e.g., such as anchored to a mitral valve annulus) can increase the likelihood of converting a tachyarrhythmia as compared to using only a single unipolar or bipolar electrode assembly in the right atrium (such as provided by a pacemaker using a "tethered" intravascular lead system). More electrostimulation sites can more readily disrupt the one or more conduction pathways followed by a reentrant depolarization waveform, since such pathways are more likely to be near one of the multiple electrostimulation sites. Also, the present inventors have recognized, among other things, that using a plurality of electrostimulation electrodes dispersed at various locations about the left or right atria, or both, can help increase the likelihood of inhibiting, preventing, regulating, or terminating an SVT, and may enable pain-free cardioversion of SVTs. Such cardioversion might be pain free by keeping the energy delivered to each electrostimulation location below a pain threshold of a patient while still achieving a sufficient electric field intensity across a region of cardiac tissue to cause a depolarization throughout the region, in bulk.

In certain patients, ablation or other surgical procedures (e.g., a Cox maze procedure) can be performed, such as to reduce an occurrence of or eliminate one or more atrial arrhythmias. However, such surgeries can permanently impair conduction through regions that have been incised or ablated. Also, certain patients can have damaged conduction paths within one or both atria, such as due to scarring around or within tissue that has experienced a previous myocardial infarction. The present inventors have recognized, among other things, that the one or more electrostimulation electrode assemblies can be used to provide one or more atrial pacing therapies such as bradyarrhythmia therapy or atrial resynchronization therapy. Such resynchronization therapy can include delivering one or more electrostimulations to multiple sites in the left or right atrium, or both, simultaneously or nearly simultaneously to spatially coordinate the depolarization such as to provide a more uniform depolarization wavefront. Such a uniform depolarization can disrupt, inhibit, or prevent one or more "circus" or reentrant wavefronts, thereby reducing a likelihood of atrial tachyarrhythmia (e.g., inhibiting or preventing an arrhythmia from developing). Such pacing therapies can be called "atrial resynchronization therapy," and can improve or restore more normal atrial conduction and contractile behavior for patients with one or more damaged conduction pathways. This can help improve atrial hemodynamics (e.g., improving atrial fill, reducing a risk of clotting due to stagnant blood in the left atrium, etc.).

Generally, intravascular leads are not chronically implanted in the left heart chambers, which risks clotting and mechanical dislodgement due to the more significant motions, acceleration and impingement of cardiac tissue on the lead and electrode assembly, when implanted endocardially in a left ventricle or a left atrium. Wireless electrostimulation assemblies can eliminate the need for the wired connection between the pulse generator assembly and an electrode assembly at a pacing site. Generally, pacing energy can be wirelessly supplied to the site from a tiny rechargeable battery located in the body of the wireless pacing electrode. This can enable an autonomous pacing assembly, but size considerations can result in frequent (e.g., daily) battery recharge, such as via wireless magnetic induction. Further, constructing various wireless pacing devices using a high magnetic permeability material, such as in ferrite-core inductors, can present a compatibility problem with magnetic resonance imaging (MRI) equipment.

In an example, the present apparatus can provide electrostimulation at patient implant locations where using intravascular lead-wires is problematic, or to electrostimulate at multiple sites that are separate and distinct from the location of a controller that transmits wireless energy to wireless electrostimulation apparatuses at the sites.

The present wireless electrostimulation apparatus can, in certain examples, also improve the range of wireless coupling, such as for wireless power transmission, or for wireless communication of information. For example, such range can be several centimeters for electrostimulation applications. This can involve using one or more inductor core materials having lower relative magnetic permeability than ferrite or using a tuned receiver design, or both. In an example, multiple wireless electrostimulation electrode assemblies can wirelessly receive energy used for electrostimulations from a common transmitter of magnetically-coupled energy (e.g., an inductive transmitter) with limited loss in efficiency as compared to using a single wireless electrostimulation assembly.

In certain examples, the wireless electrostimulation power transmitter can be located either subcutaneously within the patient, or included as part of an external device, such as a hospital bed, operating table, hand-held device, physician programmer, hat or clothing, or in one or more other locations. For a subcutaneously-implanted controller/transmitter (such as an implantable cardiac rhythm management device), explanting the controller/transmitter unit can permit replacing a battery in the controller/transmitter, without explanting the separate wireless electrostimulation electrode assemblies. Enhanced efficiency of wireless coupling of electrostimulation energy, such as from resonant coupling between the controller/transmitter and the one or more receiving wireless electrostimulation assemblies can increase the time between rechargings or battery replacements. For an external inductive transmitter, distance between the controller/transmitter and the one or more receiving wireless electrostimulation electrode assemblies can be increased, such as using resonant coupling to transmit electrostimulation energy therebetween.

The wireless electrostimulation electrode assemblies can be implanted at or near a cardiac location (e.g., such as within one or more blood vessels, or entirely within a heart chamber), and can include an expandable inductive loop antenna. In certain examples, during implantation, the expandable loop can be initially collapsed, folded, or compressed, such as to allow easier implant (such as via a delivery catheter through an intravascular route), and then unfolded, expanded, opened, or uncompressed to achieve a larger loop area, and hence greater coupling to the inductive transmit antenna. In a cardiac pacing example, an inductive transmit antenna can be incorporated into a cardiac lead system, and can be configured to expand, unfold, or open when implanted at a desired location, such as in the right side of the heart (e.g., in the right atrium or the right ventricle at or near a location accessible by a pacemaker or defibrillator intravascular lead).

In an example, a wireless electrostimulation electrode assembly can be configured to be implanted in a heart at a mitral valve annulus. In certain examples, the wireless electrostimulation electrode assemblies can include one or more electrode assemblies including an expandable mechanical support and an electrostimulation circuit. In certain examples, the expandable mechanical support can be sized and shaped to anchor an associated wireless electrostimulation electrode assembly in a blood vessel, such as a pulmonary vein, a vena cava (inferior or superior), a coronary sinus, or one or more other blood vessels.

FIG. 1 illustrates generally an example of a sectional view of a heart 102, showing an example of a wireless electrostimulation apparatus 100 including a wireless electrostimulation electrode assembly 110 implanted within the heart 102 at a mitral valve annulus, where an anterior leaflet 178A and a posterior leaflet 178B terminate in the left atrium 174. In certain examples, the wireless electrostimulation electrode assembly 110 can include an electrostimulation circuit 140 electrically connected to one or more electrically conductive electrodes, such as a first electrode 150 and a second electrode 160 located at or near cardiac tissue of the heart 102 to electrostimulate the tissue. In an example, the first electrode 150 can be an anode and the second electrode 160 can be a cathode, such as to form a closed electrostimulation circuit conductively coupled to cardiac tissue. In certain examples, one or more forms of wireless energy can be provided, such as wireless energy from a location within the heart 114A, or wireless energy from a location outside the heart 114B, and at least some of the wireless energy 114A-B can be received by the electrostimulation assembly 110. In an example, at least some of the wireless energy 114A-B can be provided as an electrostimulation to the heart 102, such as using the first electrode 150 and the second electrode 160, and the electrostimulation circuit 140. In certain examples, the wireless energy from a location within the heart 114A can be provided by one or more other implantable assemblies contained entirely within the heart, such as a battery-operated controller and transmitter. In certain examples, the wireless energy from a location within the heart 114A can be provided by a transmitter located on a cardiac rhythm management device lead system, such as located within a right atrium 170, a right ventricle 172, a location within a left ventricle 176, a coronary sinus near the left ventricle 176, or from one or more other locations. In certain examples, the wireless energy from a location outside the heart 114B can be provided from a subcutaneous location, such as from a subcutaneous lead system or transmitter attached to or part of a cardiac rhythm management device, or provided by a transmitter located outside the patient body, or from one or more other locations. In certain examples, the wireless energy from a location within the heart 114A or from a location outside the heart 114B can include acoustic energy (e.g., ultrasonic energy), optical energy, electromagnetic energy (e.g., electric field energy, magnetic field energy, or an electromagnetic wave), or one or more other forms of energy. In an example, a body of the wireless electrostimulation electrode assembly 110 can include an expandable mechanical support that is sized, shaped, or otherwise configured to anchor the assembly 110 at the mitral valve annulus.

Figure 2:
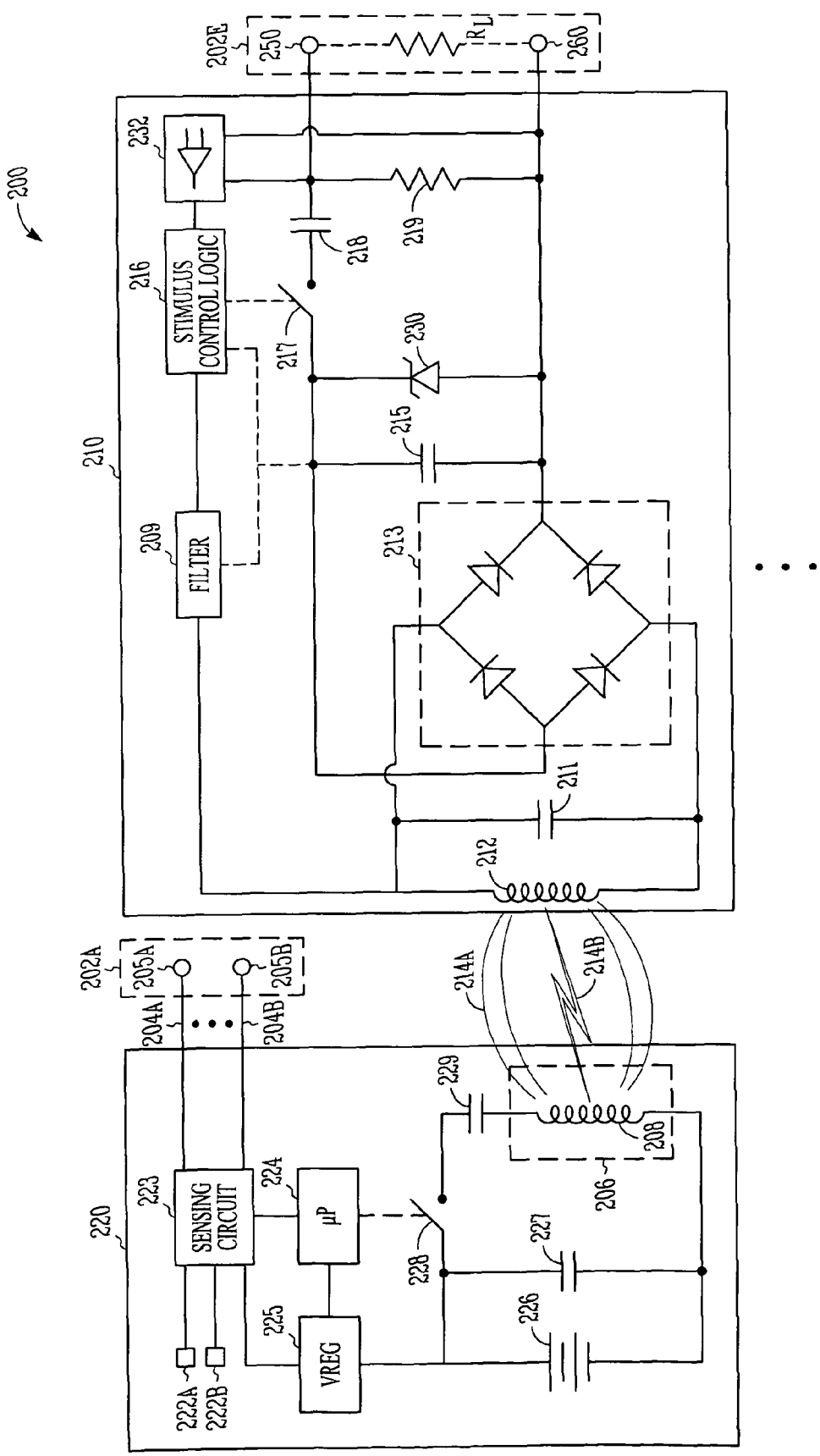
FIG. 2 illustrates generally an example of a schematic of a controller, transmitter, and a wireless electrostimulation electrode assembly.

FIG. 2 illustrates generally an example of a schematic of a wireless electrostimulation apparatus 200 including a controller/transmitter 220, and a wireless electrostimulation electrode assembly 210. The example in FIG. 2 shows a controller/transmitter 220 that can include a battery 226, a voltage regulator 225, and a microprocessor 224. In certain examples, the microprocessor 224 comprises an input-output (I/O). A switch 228 can be coupled to the microprocessor 224 using the input-output, such as to control current flow from the battery 226 or an optional energy storage device such as a capacitor 227 to an inductive antenna 206. In an example, the inductive antenna can include a wire loop inductor 208. In another example, the inductive antenna 206 can include multiple wire loops, at least some of which can be configured to be offset from each other or otherwise configured or arranged to generate two or more magnetic fields that can be spatially orthogonal to one another, such as to reduce orientation sensitivity of wireless energy transmission or wireless information communication using the inductive antenna 206. A tuning element 229 can be included, such as to allow a range of frequencies to be selected at which magnetically-coupled energy 214 will be generated by the inductive antenna 206. The resulting inductance-capacitance (LC) circuit can form a resonant "tank" circuit, which can have an operable range of resonant frequencies selected from a range of 300 KHz to 10 MHz, but selected below the self-resonant frequency of the inductor 208 comprising the inductive antenna 206.

Certain examples of the tuning element 229 can include, but are not restricted to, a capacitor, a variable-capacitance diode (e.g., "varicap" diode), an active circuit modeling a capacitor of a selected value, or the like. In some examples, the switch 228 and the tuning element 229 can be replaced, such as by a combination of a voltage-controlled oscillator and power amplifier coupled to directly drive the inductive antenna 206, such as to generate the magnetically-coupled energy 214 at a specified range of frequencies. The switch 228 can be implemented either mechanically, such as using a microminiature relay, or as solid-state device (e.g., FET, BJT, IGBT, SCR, thyristor, or the like). In certain examples, the regulator 225, the microprocessor 224, the sensing circuit 223, and the switch 228 can be co-integrated in a single integrated circuit or multi-chip module package. The "microprocessor" can include, among other things, a microcontroller including one or more of a volatile or non-volatile memory, multiple input/output channels, an analog-to-digital converter, a power supply, a digital-to-analog converter, or one or more other circuits, modules, or components that, in an example, can be co-integrated in a single integrated circuit, a single circuit package, a multi-chip module package, a hybrid, a polyimide flex-circuit assembly, or the like.

In certain examples, the initiation, timing, duration, or frequency range of the magnetically-coupled energy 214 can be controlled by the microprocessor 224, which can be provided with input from a sensing circuit 223. In an example, the sensing circuit 223 can be coupled to one or more electrodes 204A, 204B in contact with tissue, or implanted subcutaneously, such as within or near cardiac tissue 202A. In an example, the wireless energy transmission source can be external to the body, and the electrodes 204A, 204B can be coupled to the skin of the patient (e.g., to measure an electrocardiogram). In an example, the controller/transmitter 220 can be included in an implantable cardiac rhythm management device that can include one or more sense electrodes 222A, 222B coupled to the sensing circuit. In an example, the one or more of the sense electrodes 222A, 222B can be disposed on the housing of the controller/transmitter 220. In an example, the controller/transmitter 220 can include an arrhythmia detector (such as using the microprocessor 224) configured to use information provided by the one or more sense electrodes 222A, 222B or other sensing information, such as to detect an arrhythmia. In an example, such information can be used to control one or more wireless electrostimulation electrode assemblies 210, such as to provide coordinated electrostimulation to inhibit, terminate, or regulate the detected arrhythmia.

The magnetically-coupled energy 214 can be generated for either (or both) transferring the operating or electrostimulation energy 214A to the wireless electrostimulation electrode assembly 210, or information communication 214B with the wireless electrostimulation electrode assembly 210. In an example, a first range of frequencies can be established for wireless energy transfer, and a second range of frequencies can be established for commanding the wireless electrostimulation electrode assembly 210 to deliver an electrostimulus).

In the example shown in FIG. 2, a filter 209 can be configured to discriminate between the operating energy 214A and the information communication 214B. For example, the filter 209 can be configured to detect a particular range of frequencies included in the communication 214B captured by the wireless electrostimulation electrode assembly 210, such as by using an inductive pickup 212. The filter 209 can be coupled to stimulus control logic 216. In certain examples, the logic 216 can be configured to inhibit or to initiate tissue electrostimulation, such as in response to the filter 209 detecting one or more specified signals. The filter 209 can include, in certain examples, a band-pass filter, which can be coupled to a threshold comparator. In certain examples, the filter 209 can include a digital demodulator. In certain examples, communication 214B can be encoded digitally and can include (or be transmitted concurrently to) operating energy 214A being wirelessly communicated to the wireless electrostimulation electrode assembly 210. Examples of digital encoding of communication 214B can include, but are not restricted to, on-off keying, amplitude-shift keying, phase-shift keying, frequency-shift keying, or the like.

In certain examples, the combined capacitance of the tuning element 229 and actual or parasitic capacitances of the inductive antenna 206 can vary when the wireless energy transmission source is implanted in or near tissue 202E. The effect of tissue interaction with the system can be reduced by at least partially surrounding the inductive antenna 206 or the inductive pickup 212 with a protective material or encapsulant (e.g., silicone or one or more other encapsulating compounds). Such encapsulation can inhibit or prevent tissue 202E or liquid (e.g., blood or one or more other bodily fluids) from penetrating into the cavities between individual turns of the windings of the inductive pickup 212 or the inductive antenna 206, which would otherwise increase the effective relative dielectric constant seen by the pickup 212, or the antenna 206.

In certain examples, the microprocessor 224 can be configured to adjust the capacitance of the tuning element 229, or to adjust the frequency of a corresponding voltage-controlled oscillator, such as to achieve a desired level of efficiency in coupling to the wireless electrostimulation electrode assembly 210. In an example, a cardiac pacing electrostimulus can be applied, such as using electrodes 250 and 260, and the evoked response can be observed, such as using the sensing electrodes 205A, 205B, the leads 222A, 222B, an external electrocardiogram sensing apparatus, or one or more other sources of physiologic information. The tuning element 229, or a corresponding frequency synthesizer, can be adjusted by the microprocessor 224, such as to vary the generated range of frequencies of magnetically-coupled energy 214, for example, until a desired or reliable "capture," (e.g., activation of cardiac tissue resulting from electrostimulation) is observed.

In an example, the wireless electrostimulation electrode assembly 210 can include an inductive pickup 212 and an optional discrete tuning element 211. In an example, the value of the capacitance of the tuning element 211 can be selected before implanting the wireless electrostimulation electrode assembly, such as to achieve a desired resonant frequency when implanted, such as when surrounded by blood or muscle tissue. In certain examples, to reduce the size of the wireless electrostimulation electrode assembly 210, a discrete capacitor, such as used for tuning element 211, can be omitted, and the capacitance used to achieve resonance of the inductive pickup 212 can be provided by the parasitic capacitance of the physical coil structure of the inductive pickup 212 (for example, the inter-winding capacitance), or one or more other sources of distributed capacitance.

In an example, the magnetically-coupled energy 214A can be rectified, such as by a full-wave rectifier 213, as shown in the example in FIG. 2, or by a half-wave rectifier, which can save space by reducing the number of diode components used in the wireless electrostimulation electrode assembly 210. Rectified energy can be stored in an optional capacitor 215, such as shown in the example in FIG. 2. In an example, the capacitor 215 can act like a filter capacitor, such as to help suppress ripple voltage. Stimulus control logic 216 can be coupled to a switch 217. The switch 217 can include a solid-state device (e.g., FET, BJT, IGBT, SCR, thyristor, etc.). In an example, such as to reduce the size of the wireless electrostimulation electrode assembly 210, one or more of the filter 209, the logic 216, the switch 217, or the rectifier 213, or one or more other circuits, components, or modules can be co-integrated into a single integrated circuit package, or for example, into a multi-chip module or the like similar to that described above for the controller/transmitter 220.

In certain examples, multiple storage devices 215 and switches 217 can be used, such as to arrange stored voltages in a desired series, parallel, or series-parallel combination, for example, such as to achieve an electrostimulus peak voltage in excess of the maximum voltage stored on a single capacitor 215 using operating energy 214A.

In an example, a direct-current (DC) blocking device 218 can be used to inhibit a DC-stimulus component from being coupled to the electrostimulus electrodes 250, 260. The electrostimulus electrodes 250, 260 can be conductively coupled to the muscle tissue 202E to be electrostimulated (e.g., myocardial tissue). In an electrostimulation example, the electrode 250 can be used as the cathode and the electrode 260 can be used as the anode.

The blocking device 218 and the shunt device 219 can form a high-pass network configured such that the upper cutoff frequency (or resulting time-domain pulse shape) can be selected or even programmably adjusted, such as to form or shape a desired electrostimulus waveform. In an illustrative example, the blocking device 218 can be selected as a capacitor having a capacitance of about 1 microFarad, and the shunt device 219 can be selected as an approximately 5 kiloOhm resistor, such as to achieve a desired cardiac tissue electrostimulation pacing pulse.

The present inventors have recognized that, among other things, tissue and body fluid can absorb and disperse inductive energy, and that such absorption and dispersive effects can rapidly increase at frequencies greater than 100 KHz. These effects can severely limit the range and maximum achievable efficiency of typical magnetic coupling schemes. One technique for decreasing such losses can be to substantially or completely surround the inductive antenna 206 or inductive pickup 212 with a high relative permeability magnetic material, such as an iron-powder core, a ferrite material, or the like. Such materials can effectively magnify the magnetically-coupled energy density experienced by a nearby winding structure, at a given incident magnetic field intensity.

The high relative magnetic permeability of such materials can render the resultant implantable device assemblies incompatible with magnetic resonance imaging (MRI) equipment. Locally-induced forces or torques (e.g., induced in single components) associated with the strong bias field present near operating MRI equipment could result in mechanical damage to the inductive antenna 206 or the inductive pickup 212 assemblies if they incorporate a high relative magnetic permeability material.

MRI equipment can also induce large voltages, across the terminals of the inductive antenna 206 or the inductive pickup 212, and large currents. This can induce an internal temperature rise. This can damage (e.g., by electrical short-circuiting or dielectric failure) inductors or other components electrically coupled thereto, or can thermally damage surrounding tissue 202E.

In an example, one or more protection devices (e.g., discharge tubes, gaps, solid-state transient-suppression devices) can be additionally or alternatively included to inhibit or prevent MRI-related electrical damage. A small wireless electrostimulation electrode assembly 210 is generally desired (e.g., to allow intravascular introduction and placement) and such additional protection devices can use additional space and may not mitigate the MRI-induced forces and torques.

The present inventors have also recognized, among other things, that ferrite core materials can also have other limitations. For example, internal loss mechanisms can preclude using ferrite as core material for highly-tuned inductors at frequencies above a few MHz. This can prevent the resonant "tank circuit" in the inductive transmit network or inductive receiver network from achieving high power coupling efficiencies, since the quality factors ("Q") of both networks are limited by the resistive damping effects of increasing losses within the ferrite core material.

By contrast, the present inventors have recognized that, in a different approach, the core materials or mechanical supports surrounding the inductive antenna 206 or the inductive pickup 212 can include one or more materials other than ferrites, such as one or more materials having a relative magnetic permeability less than 1.1. In certain examples, the inductive antenna 206 or the inductive pickup 212 can be surrounded by, encompassed by, or located near a material or a mechanical support having a relative magnetic permeability substantially equal to 1, such as air, one or more bodily tissues (e.g., muscle, fat, bone, etc.), or one or more bodily fluids such as blood. In these examples, an effective relative magnetic permeability seen by the inductive antenna 206 or the inductive pickup 212 can be substantially equal to 1, such as such as representing an inhomogeneous medium around the inductive antenna 206 or the inductive pickup 212.

Materials, such as shape-memory Nickel-Titanium (NiTi or Nitinol) compounds, are effectively non-ferromagnetic and can have other beneficial mechanical properties. For example, the shape-memory property can be used to provide self-expansion (e.g., after implant) of the loop antenna 206 or the inductive pickup 212. Increasing or maximizing the area of a loop forming an inductive antenna 206, or inductive pickup 212, can enhance the mutual coupling of two nearby such inductive devices. In some examples, such a shape-memory material can be used as a mechanical support, such as to provide an expansion force to expand a wound coil that is configured to be used as either an inductive transmit antenna (e.g., inductive antenna 206) or as an inductive receiver (e.g. inductive pickup 212). Such materials can also help mitigate ferrite efficiency loss and allow more efficient coupling of time-varying magnetic flux through tissue, such as at frequencies up to several MHz. The term "air core" can be used to describe inductive transmitter 208 and inductive pickup 212 structures that do not have a ferrite core within a wound loop of such structures, even though the actual construction of such devices might include non-ferromagnetic metallic support structures and, when implanted, tissue or bodily fluid may be present within the core of the inductive transmitter 208 or inductive pickup 212.

In an illustrative example, a mathematical analysis of a simplified combination of the controller/transmitter 220 and wireless electrostimulation electrode assembly 210 can be used to estimate power coupling efficiency, $\eta$, and electrostimulus output voltage magnitude, $|V_L|$. The combination of the switch 228, and the battery 226 can be represented as an AC voltage source operating at angular frequency $\omega$, and peak output voltage $V_0$. The inductive antenna 206 can be modeled as a combination of an ideal inductor, L, 208 in series with a transmit circuit resistance R. The tuning element 229 can be modeled as a capacitor, C. The transmit circuit impedance can be represented as $Z=R+i(\omega L-1/\omega C)$, in which $i=\sqrt{-1}$. At resonance, $C=1/\omega^2 L$, and $Z=R$. The imaginary components, due to the reactances of the capacitor and inductor, can cancel each other (unity power factor).

Similarly, for the electrostimulation circuit that can be included in the wireless electrostimulation electrode assembly 210, the inductor 212 can be modeled as $L_1$, and its corresponding loss as resistance "r" in series with $L_1$. The tuning element 211 can be modeled as a parallel capacitor $C_1$, and the tissue load 202E appearing across electrostimulus electrodes 250, 260 can be modeled as $R_L$. Neglecting the rectifier 213, the switch 217, the shunt capacitor 215, the blocking device 218, and the shunt resistor 219, the receiver inductive pickup impedance can be represented as $Z_1=r+i\omega L_1$, and the impedance associated with the tissue load and tuning element can be represented as $Z_L=R_L/(1+i\omega R_L C_1)$.

For the wireless electrostimulation electrode assembly 210, this can be represented as a lossy inductive pickup $Z=r+i\omega L_1$ in parallel with a load represented by $Z_L=R_L/(1+i\omega R_L C_1)$. The total parallel impedance $Z_2=r+R_L/(1+(\omega R_L C_1)^2)+i[\omega L_1-\omega R_L^2 C_1/(1+(\omega R_L C_1)^2)]$. At resonance, $1+(\omega R_L C_1)^2=R_L^2 C_1/L_1$, and $Z_2=r+R_L/(1+(\omega R_L C_1)^2)=r[1+L_1/(rR_L C_1)]$. The magnitude of $Z_L=\sqrt{(L_1/C_1)}$.

The mutual inductance, M, of the transmit antenna 206 and the inductive pickup 212 can be represented as the product of the self inductances of the two inductors 208, 212 and a coupling constant, $\kappa$: $M^2=\kappa L L_1$. Power coupling efficiency and peak output voltage at the tissue load 202E can be represented as:

$$\eta=\kappa QQ_1 x/[(1+x)(1+x+\kappa QQ_1)] \quad (1)$$

$$|V_L|=\sqrt{(R_L/R)\kappa QQ_1 x}V_0/(1+x+\kappa QQ_1) \quad (2)$$

where $Q=\omega L/R$=quality factor of transmitter, $Q_1=\omega L_1/r$=quality factor of receiver, and $x=L_1/(rR_L C_1)$. The following relation can be obtained:

$$\kappa QQ_1 \gg 1+x, \quad \eta \rightarrow x/(1+x) \quad (3)$$

and when $x \gg 1$, the power coupling efficiency, $\eta$, approaches 1 (corresponding to 100%). Thus, for small values of the coupling constant, $\kappa$, if the quality factors are sufficiently large, the power coupling efficiency can approach unity.

Generally, the wireless electrostimulation electrode assembly 210 receiver resonant frequency and quality factor $Q_1$ can vary depending on the specific implant configuration of the inductive pickup 212, and the resulting tissue and blood proximity effects on the electrical response of the inductive pickup 212. However, by actively varying the value of tuning element 229 in the controller/transmitter 220, as described previously, the controller/transmitter 220 transmitter resonant frequency can be varied, such as to compensate for changes in the wireless electrostimulation electrode assembly 210 receiver resonant frequency or to control electrostimulus amplitude or energy achieved at electrodes 250, 260.

In certain examples, if the transmitter 220 quality factor, Q, is selected to be much greater than the receiver quality factor, $Q_1$, the receiver can have a broader "tuning envelope" than the transmitter. With a broader wireless electrostimulation electrode assembly 210 receiver response characteristic, the transmitter tuning element 229 can be adjusted more easily (e.g., less precisely) to provide an operating frequency at resonance corresponding the resonant frequency of the receiver in the wireless electrostimulation electrode assembly 210 (e.g., the transmitter can be tuned to be more sharply "peaked" at resonance than the receiver, and transmitter resonant frequency can then be swept until centered on receiver resonant frequency).

In certain examples, varying the resonant frequency of the transmitter by changing the capacitance of the tuning element 229 can also control the magnitude of the electrostimulus voltage coupled to the tissue load 202E. Selecting a value for the tuning element 229 that shifts the resonant frequency of the controller/transmitter 220 away from the resonant frequency of the wireless electrostimulation electrode assembly 210 can result in decreasing maximum voltage, $|V_L|$, coupled to the tissue load 202E. This can reduce the size of the wireless electrostimulation electrode assembly 210 by eliminating or reducing the complexity of logic 216 and the switch 217 such as by allowing electrostimulation amplitude control to be accomplished by the controller/transmitter 220.

In certain examples, the operating energy 214A can be limited in duration or maximum amplitude such as to avoid tissue heating or regulatory limits for average or instantaneous power transmitted through tissue. The resulting rectified energy can be integrated or otherwise accumulated by, for example, the capacitor 215. $|V_L|$ can, for instance, be established by a series- or shunt-regulation component such as a Zener diode 230.

In certain examples, the Zener diode 230 can be used to simplify or eliminate the stimulus control logic 216 and the switch 217 when a pulse-width modulation (PWM) scheme is used at the controller/transmitter 220. A microprocessor, state machine, timing logic, and the like can be omitted from the wireless electrostimulation electrode assembly 210 to reduce complexity, physical volume, etc.

In one example, the stimulus control logic 216 can still be used to inhibit electrostimulation delivery to the tissue load 202E (e.g., by opening the switch 217 when an intrinsic event is sensed), but is not required to control the level of electrostimulation energy content delivered to the tissue load 202E.

In certain examples, the operating energy 214A can be established at a specific burst duration (e.g., a burst can be a square pulse envelope commencing a sequence of multiple resonant oscillations). The duration or pulse width of the burst of operating energy 214A can be related to the energy content delivered to the tissue load 202E when the diode 230 is clamping the voltage across the capacitor 215.

If the tissue 202E is modeled as a cardiac tissue load having a resistance $R_L$=1 kiloOhm in parallel with a series-combination of a 1 kiloOhm resistor ($r_L$) and a 1 microFarad capacitor ($C_L$), a cardiac tissue electrostimulation pacing pulse of greater than 4V peak amplitude, $|V_L|$, can be achieved using a resonant frequency of 1 MHz.

In an illustrative example, at a leading edge of a cardiac tissue electrostimulation pulse, the load capacitor can be represented effectively as a short circuit, and the AC resistance of the model cardiac tissue load 202E is equal to around 500 ohms (1 kiloOhm in parallel with 1 kiloOhm).

In certain examples, the burst duration of the operating energy 214A can be controlled by the microprocessor 224 and the switch 228 at the controller/transmitter 220 to achieve a desired energy content coupled to the tissue load 202E.

A theoretical voltage delivered across a cardiac tissue capacitance, $V_{CAP}$, can be represented as:

$$V_{CAP} = V_{CLAMP}[1 - e^{-w/r_L C_L}] \quad (4)$$

where $V_{CLAMP}$ represents the voltage clamping threshold of the diode 230, and w represents the burst pulse duration (in seconds). For small burst pulse durations, $V_{CAP}$ can be approximated as:

$$V_{CAP} = V_{CLAMP}[w/r_L C_L] \text{ for } w << r_L C_L \quad (5)$$

In an example, $V_{CLAMP}$ can be 5.6V (e.g., established by the Zener diode 230), w can be 775 microseconds, $r_L = R = 1$ kiloOhm, and C=1 microFarad. Using EQUATION 4, $V_{CAP}$ can be computed as approximately 3 Volts. In another example, w can be 1250 microseconds, and $V_{CAP}$ can be computed as approximately 4 Volts.

In certain examples, the volume occupied by wireless electrostimulation electrode assembly 210 can be decreased by limiting the total energy stored, for example, the capacitor 215. An estimate of the desired stored energy for various electrostimulation pulses can be made. For example, if $R_L = 500$ Ohms, and $|V_L| = 2.5V$, a square-wave pulse of duration T=0.4 milliseconds can correspond to a stored electrostimulation energy of $T|V_L|^2/R_L = 5$ microjoules.

The capacitor 215 can be specified as a capacitor=$C_S$, in microFarads. The energy stored in the capacitor 215 can be represented as $\frac{1}{2} C_S |V_L|^2$. The number of electrostimulation delivery cycles that the energy stored in the capacitor 215 can deliver can be represented as: the energy stored on the capacitor=$\frac{1}{2} C_S |V_L|^2$, divided by the electrostimulation energy consumed by a single electrostimulation cycle delivered to the tissue impedance=$T|V_L|^2/R_L$. Thus, the number of cycles that capacitor 215 can supply can be represented as = $R_L C_S/2T$.

Tradeoffs can be made between the capacitor 215 value $C_S$, load resistance $R_L$ and, for example, pulse width, to achieve a desired wireless electrostimulation electrode assembly 210 volume and a desired electrostimulation duration, for instance, during an interval when the inductive operating energy 214A is absent or insufficient.

For example, the number of desired electrostimulation cycles can be=N, and value for capacitor 215 to provide N electrostimulation cycles can be represented as $C_S = 2TN/R_L$. In an example, an electrostimulation pulse duration can be specified as T=0.4 msec, the load resistance can be $R_L = 500$ Ohms, and the capacitance $C_S$ can be represented for N=1 as $C_S = 1.6$ μF. A low voltage 1.6 μF capacitor 215 can be small (e.g., sub-millimeter dimensions on each axis).

In certain examples, back-up storage can be desired for patient protection (e.g., to provide continued electrostimulation for a limited duration in the temporary absence of the operating energy 214A). A heart rate can be specified=$H_R$ in Hertz, a number of cardiac cycle to be paced in a total time=$T_{stored}$, in seconds, can be represented=$H_R T_{stored}$, and the size of the capacitor to store a corresponding amount of energy can be represented, $C_S = 2TH_R T_{stored}/R_L$. For example, one hour=3600 sec of stored electrostimulation energy and a heart rate of 72 beats per minute or 1.2 Hz can be specified, resulting in, for example, a number of pacing electrostimulation cycles $H_R T_{stored} = 4320$, and a total stored energy=21.6 milliJoules. The tissue impedance $R_L$ can be specified as 500 Ohms and pulse width can be specified as T=0.4 msec, and the capacitance 215 can be represented $C_S = 6912$ μF. Such a capacitor can occupy several cubic millimeters of volume in the receiver circuit.

In certain examples, a compromise between the capacitor 215 value $C_S$ and the physical size of the capacitor 215 can be made. In an illustrative example, the capacitor 215 can be specified, $C_S = 320$ μF, and electrostimulation pulses can be specified, $|V_L| = 2.5$ volts.

In another illustrative example, the total energy stored on capacitor 215 is 1 milliJoule, and can be enough energy to deliver 200 electrostimulation cycles of pulse width T=0.4 msec to into a tissue load $R_L = 500$ Ohms. In another illustrative example, capacitor 215 can be specified $C_S = 320$ μF and the electrostimulation cycle rate of 72 electrostimulation cycles per minute can result in continued electrostimulation delivery, for approximately 2.8 minutes, by wireless electrostimulation electrode assembly 210, after the operating energy 214A to $C_S$ is inhibited or interrupted.

The capacitor 215 can also be specified to accommodate the quiescent power consumed by, for example, the stimulus control logic 216 comprising a microprocessor, which can be very small depending upon the device used, but in some cases can be comparable to, or larger than, the average pacing power. In certain examples, the power consumed by the wireless electrostimulation electrode assembly 210 can be reduced if the stimulus control logic 216 and the filter 209 are omitted and the switch 217 is permanently closed or omitted. For certain examples, the capacitor $C_S$ can be a filter capacitor, and the operating energy 214A received by the wireless electrostimulation electrode assembly 210 can be rectified and delivered directly to the tissue load (e.g., the delivered electrostimulation pulse width can correspond to the width of a transmitted energy 214A burst pulse, provided that the time constant $\tau = C_S R_L$ is less than about one half of the pulse width). In certain examples, such direct conversion of energy 214A into an electrostimulation delivery can be achieved when $C_S < 0.4$ μF (e.g., corresponding to an electrostimulation pulse width of T=0.4 msec and load $R_L = 500$ Ohms).

In certain examples, the sensing circuitry 232 can be coupled to the cardiac tissue 202E to provide physiologic information to stimulus control logic 216 in response to sensed potentials detected by the sensing circuitry 232. Signaling to the stimulus control logic 216 by the sensing circuitry 232 can occur in response to intrinsic tissue activity (e.g., the sensing circuitry 232 establishes a threshold level or window and intrinsic activity can cause a voltage fluctuation exceeding a threshold level or window resulting in a threshold crossing signal to the stimulus control logic). The stimulus control logic 216 can inhibit electrostimulation using the switch 217 in response to, for example, detection of sensed events provided by the sensing circuitry 232.

In certain examples, a shunt device 219 can also provide charge neutralization. Charge neutralization can include providing a path between the electrostimulus electrodes 250, 260 to slowly discharge an afterpotential occurring during or after an electrostimulation, resulting in a net neutral charge delivered by the electrostimulation electrodes 250, 260. For the example of a pacing waveform described above, charge neutralization can be observed as a smaller amplitude negative-phase pulse of longer duration following the positive-phase cardiac tissue electrostimulation pulse. In certain examples, the wireless electrostimulation electrode assembly 210 can include multiple electrostimulation output blocks electrically connected to multiple electrostimulation electrodes 250, 260. In certain examples, one or more capacitors 215, can be coupled to one or more respective cathode electrodes 250, such as through one or more respective switches 217. In an example, the one or more cathode electrodes 250 can use a commonly-shared anode electrode 260.

Figure 3:
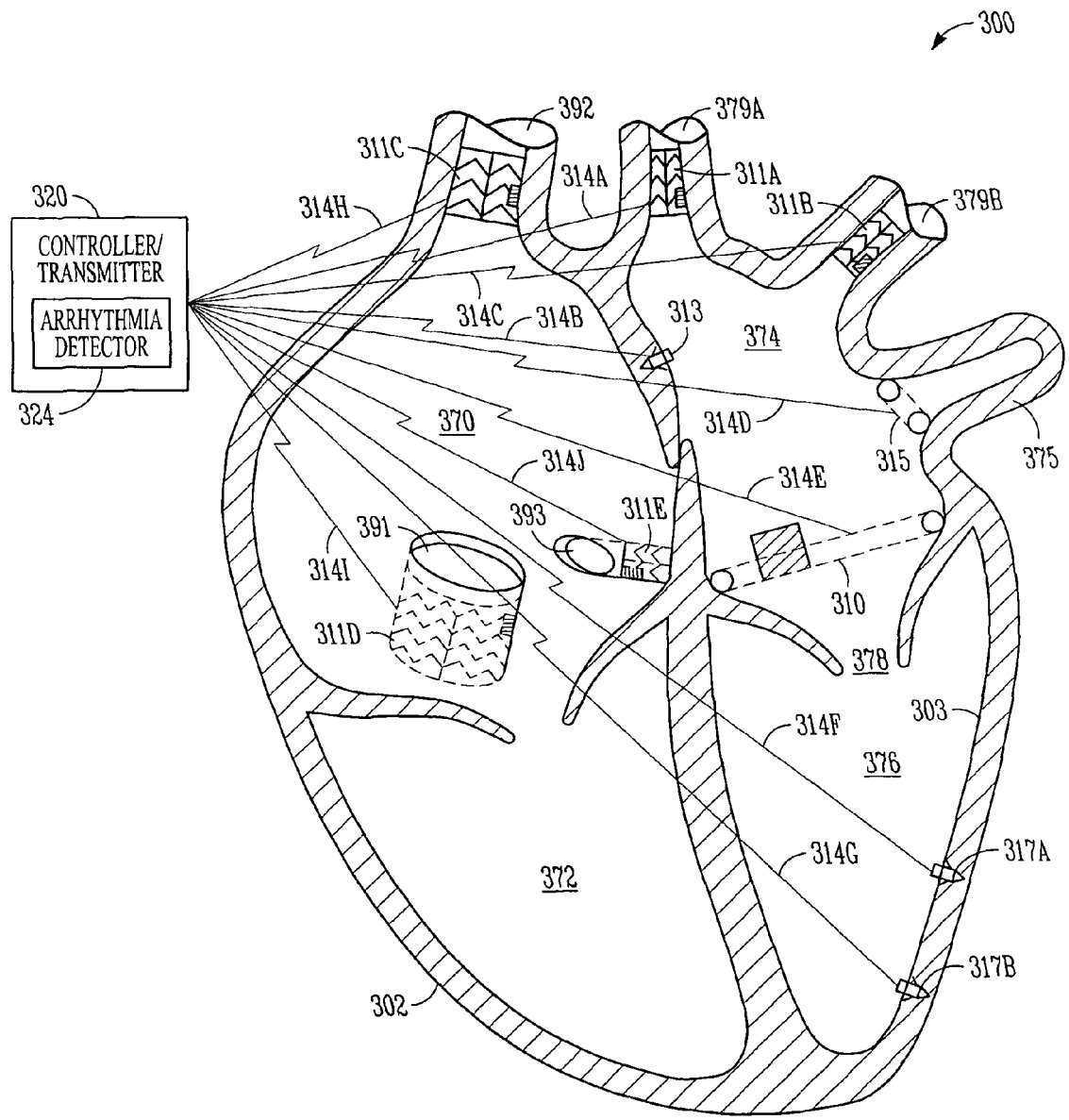
FIG. 3 illustrates generally an example of an apparatus including a plurality of wireless electrostimulation electrode assemblies at respective implant locations within a heart and within respective blood vessels.

FIG. 3 illustrates generally an example of an apparatus 300 including a plurality of wireless electrostimulation electrode assemblies at respective implant locations within a heart 302 and within respective blood vessels.

In the example of FIG. 3, a first wireless electrostimulation electrode assembly 310 can be located within a heart 302 at a mitral valve 378 annulus, as shown and discussed above in FIG. 1. A controller/transmitter 320 can include one or more wireless couplings to one or more wireless electrostimulation electrode assemblies, such as a wireless coupling 314E to the first assembly 310. In an example, the first assembly 310 can receive operating energy or communicate (e.g., control information, sensing information, a signal to initiate an electrostimulation, or one or more other forms of information) using the wireless coupling 314E.

In certain examples, one or more additional wireless electrostimulation electrode assemblies can be implanted at other locations within the heart, or within one or more blood vessels, resulting in a plurality of wireless electrostimulation electrode assemblies available to deliver one or more coordinated electrostimulations, such as to locations within a right atrium 379, a left atrium 374, or a left ventricle 376. In an example, an apparatus including the plurality of wireless electrostimulation electrode assemblies can also include one or more intravascularly-introduced endocardial leads, such as to provide electrostimulation to the right ventricle 372, the right atrium 379, or one or more other locations.

In an example, a second wireless electrostimulation electrode assembly 315 can be located at or near an ostium of left atrial appendage 375. Such a second assembly 315 can also be used, for example, to partially or completely occlude or block the opening to the left atrial appendage 375. In this example, the second assembly 315 can include an expandable mesh, or screen, or other semi-permeable or impermeable structure to prevent a blood clot or other debris within the left atrial appendage 375 from being released elsewhere into the heart 302, or vasculature (e.g., see FIG. 7). In an example, a third wireless electrostimulation electrode assembly can be located at a right atrial appendage. In an example, the third wireless electrostimulation electrode assembly can be configured to occlude or block the opening to the right atrial appendage. In certain examples, one or more wireless electrostimulation electrode assemblies can be located in one or more pulmonary veins, such as a fourth wireless electrostimulation electrode assembly 311A located within a right pulmonary vein 379A, or a fifth wireless electrostimulation electrode assembly 311B located within a left pulmonary vein 379B. In certain examples, the fourth or fifth assemblies 311A, 311B can receive operating energy or communicate with the controller/transmitter 320 using respective wireless couplings 314A, 314C. In certain examples, one or more wireless electrostimulation electrode assemblies can be located in the vena cava, such as a sixth wireless electrostimulation electrode assembly 311C located in a superior vena cava 392, or a seventh wireless electrostimulation electrode assembly 311D located in an inferior vena cava 391. In certain examples, the sixth or seventh assemblies 311C, 311D can receive operating energy or communicate with the controller/transmitter 320 using respective wireless couplings 314H, 314I. In certain examples, a body of one or more intravascularly-introduced endocardial leads can occupy a vena cava after a sixth or seventh assembly 311C, or 311D is implanted, since the sixth or seventh assembly 311C, or 311D can be stent-like and need not occupy a large portion of a cross section of the vena cava.

In certain examples, an eighth wireless electrostimulation electrode assembly 311E can be located in a coronary sinus. In an example, the eighth assembly 311E can receive operating energy or communicate with the controller/transmitter 320 using a wireless coupling 314J. In an example, the eighth assembly 311E is located within the coronary sinus as closely as possible to the ostium of the coronary sinus, such as to place one or more electrostimulation electrodes in electrical contact with a muscle sleeve portion of the coronary sinus. In certain examples, if an ablation procedure has been performed near or around the ostium of the coronary sinus, the eighth assembly 311E can be used to terminate or control a reentrant arrhythmia having a focus or conduction pathway near the ostium of the coronary sinus. In certain examples, one or more wireless electrostimulation electrode "seed" assemblies can be implanted partially or completely within the myocardium of the heart 302, such as in left atrium 374, or in the left ventricle 376 where intravascularly-introduced endocardial leads are contra-indicated. In an example, the eighth assembly 313 can receive operating energy or communicate with the controller/transmitter 320 using a wireless coupling 314B. In an example, a ninth wireless electrostimulation electrode assembly 313 can be located in the atrial septal region of the heart 302. In certain examples, a tenth or an eleventh wireless electrostimulation electrode assembly 317A, 317B can be located partially or completely within myocardial tissue in the left ventricle 376. In certain examples, the tenth or eleventh assemblies 317A, 317B can receive operating energy or communicate with the controller/transmitter 320 using respective wireless couplings 314F, 314G. In an example, one or more of the wireless couplings 314A-J can use magnetically-coupled energy, such as inductive coupling, between the controller/transmitter 320 and one or more wireless electrostimulation electrode assemblies 310, 311A-E, 313, 315, 317A-B to provide operating energy to, or to communicate with, the one or more wireless electrostimulation electrode assemblies 310, 311A-E, 313, 315, 317A-B. In certain examples, one or more of the wireless electrostimulation electrode assemblies 310, 311A-E, 313, 315, 317A-B can include circuitry or components similar to the wireless electrostimulation electrode assembly 210 shown in FIG. 2. In an example, the transmitter/controller 320 can be a subcutaneous implantable medical device such as a cardiac rhythm management device. In an example, the transmitter/controller 320 can include circuitry or components similar to the controller/transmitter 220 shown in FIG. 2. In certain examples, one or more of the wireless electrostimulation electrode assemblies 310, 311A-E, 313, 315, 317A-B can be delivered into the heart or into the one or more blood vessels using an intravascular, transluminal route, such as through one or more delivery catheters. In certain examples, one or more of the wireless electrostimulation electrode assemblies 310, 311A-E, 313, 315, 317A-B can include one or more expandable mechanical supports configured to fold, collapse, or contract during delivery to an implant location, allowing the one or more wireless electrostimulation electrode assemblies to pass through the lumen of a delivery catheter when the delivery catheter is passed through one or more blood vessels. In certain examples, the wireless electrostimulation electrode assemblies 311A-E can be stent-like, as shown in FIG. 3, and can be located in one or more blood vessels so that one or more electrostimulation electrodes included with the wireless electrostimulation electrode assemblies 311A-E can be in contact with a muscle sleeve near the opening or ostium of the one or more blood vessels. In certain examples, one or more wireless electrostimulation electrode assemblies 310, 311A-E, 313, 315, 317A-B can include multiple electrodes coupled to an electrostimulation circuit included as a portion, part or component of each of the respective assemblies 310, 311A-E, 313, 315, 317A-B. In an example, the multiple electrodes can be multiple cathode electrodes included on a portion of the one or more wireless electrostimulation electrode assemblies 310, 311A-E, 313, 315, 317A-B. In an example, the multiple cathode electrodes can be located closer to the heart 302, such as contacting the muscle sleeve near the opening or ostium of the one or more blood vessels. In an example, the multiple cathode electrodes can share a common anode electrode.

In certain examples, the controller/transmitter 320 can include an arrhythmia detector 324. In certain examples, the arrhythmia detector can detect, identify, or categorize one or more arrhythmias and can provide communication or operating energy to one or more wireless electrostimulation electrode assemblies 310, 311A-E, 313, 315, 317A-B, such as to provide one or more coordinated electrostimulations to regulate, control or terminate the arrhythmia. In certain examples, the arrhythmia detector 324 can detect one or more arrhythmias using physiologic information, such as provided by one or more electrocardiogram sensing electrodes. In certain examples, the arrhythmia detector 324 can include one or more timers or comparators, such as to detect a shortened QRS duration, a shortened P-wave to QRS duration, multiple P-waves or one or more other arrhythmic indications derived from information from the one or more electrocardiogram sensing electrodes, or from other physiologic sensors. In certain examples, the arrhythmia detector can be a portion, part or component of a microprocessor, microcontroller, multi-chip module, or one or more other circuits or modules, such as shown in the controller/transmitter 220 in FIG. 2.

In some patients, one or more conduction pathways of the heart 302 can be damaged, such as due to previous myocardial infarct, disease, or one or more other acute or chronic causes or conditions. Intravascularly-introduced endocardial pacemaker or defibrillator lead systems can be incapable of use at locations near such damaged pathways. For example, such intravascular leads can be contra-indicated for use at many locations where such conduction pathway damage can occur (e.g., the left heart, or within one or more blood vessels near or within the heart.) The present inventors have recognized that a likelihood that an arrhythmia can be detected, prevented, or terminated can be increased when endocardially-implanted or vascularly-implanted wireless electrostimulation electrode assemblies are used since a greater variety of implant locations can be available compared to intravascularly "tethered" conductive electrostimulation lead systems, and such wireless assemblies can be compact and can fit entirely within a chamber of the heart or within one or more blood vessels. Studies might show that multi-site atrial pacing, including left atrial sites, at locations that can be known as "atrial fibrillation triggers," can prevent or reduce an incidence of atrial fibrillation or other atrial arrhythmias. In an example, one or more locations in each of the left and right atria can be paced simultaneously to provide "atrial resynchronization therapy." In this example, tissue can be depolarized before the arrival of an arrhythmic depolarization wavefront, and such tissue can be in a refractory period, thus breaking the propagation of the arrhythmic depolarization wavefront (e.g., preventing the depolarization wavefront from activating tissue that has been previously electrostimulated, since such tissue is in a refractory period).

In certain examples, the one or more electrostimulation electrode assemblies 310, 311A-E, 313, 315, 317A-B can be used to defibrillate the heart 302. In these examples, multi-site or distributed defibrillation, as distinct from pacing therapies, can require less total energy as compared to two pole defibrillation (e.g., defibrillation using only two electrodes). In an illustrative example, a threshold electric field intensity can be determined when two electrodes are placed across the heart (or atria in the case of AFIB). In this example, the two electrodes can reliably defibrillate the heart 302 when the threshold electric field intensity can be exceeded. The electric field in tissue can be reduced in proportion to the inverse square of the distance from a defibrillation electrode. The threshold electric field can be represented as the electric field needed to fully depolarize tissue that is farthest from an electrode. Tissue of the heart 302 can be modeled a as spherical shell of radius R, and two defibrillation electrodes can be separated by a distance $\pi R$. In an illustrative example, if an array of N electrodes can be distributed uniformly over the tissue shell, the separation between electrodes in the array can be represented by $\pi R \sqrt{(2/N)}$. In this example, a minimum electric field needed to depolarize tissue midway between the array of electrodes can be proportional to the inverse square of their separation, and thus the ratio of minimum electric field needed for N electrodes compared to the minimum electric field needed two electrodes can be represented as 2/N. Defibrillation energy can be proportional to the square of the electric field, so a ratio of defibrillation energy to be delivered between any pair of electrodes in the array as compared to two electrodes alone can be represented as $4/N^2$. In this illustrative example, since there are N/2 pairs of electrodes in the array, the total energy delivered to the array to provide defibrillation, divided by the total energy needed if only two electrodes are used, can be represented as 2/N.

In an illustrative example, a clinical requirement for painless atrial defibrillation can be that no more than one Joule total energy can be delivered to the tissue to avoid pain. In this example, if a typical defibrillation between only two implanted electrodes is 4 Joules, then a painless, one Joule, shock can be delivered using 8 distributed electrodes, with 0.25 Joules delivered between respective electrode pairs.

Figure 4A:
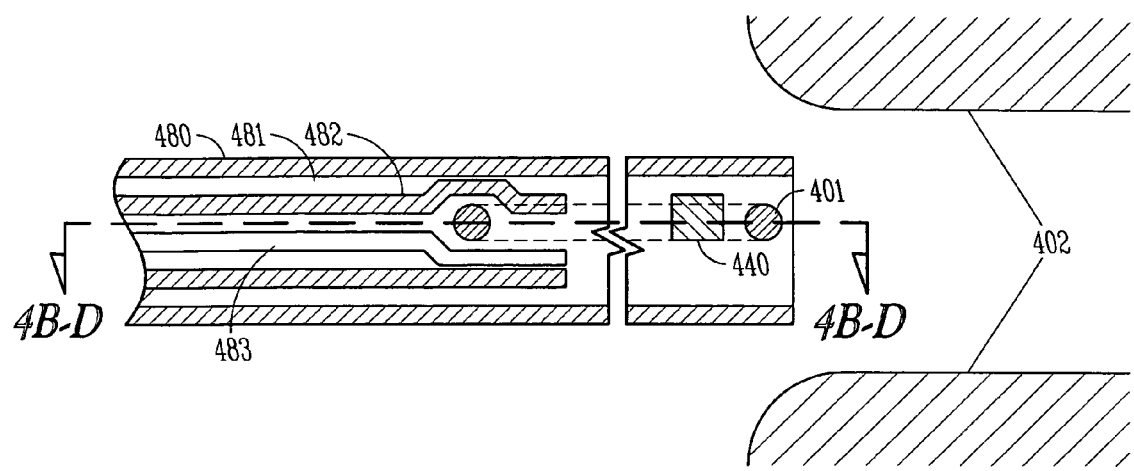
FIGS. 4A-D illustrate generally section views of an example of a system including a delivery catheter, actuator, and a wireless electrostimulation electrode assembly including an expandable mechanical support.
Figure 4B:
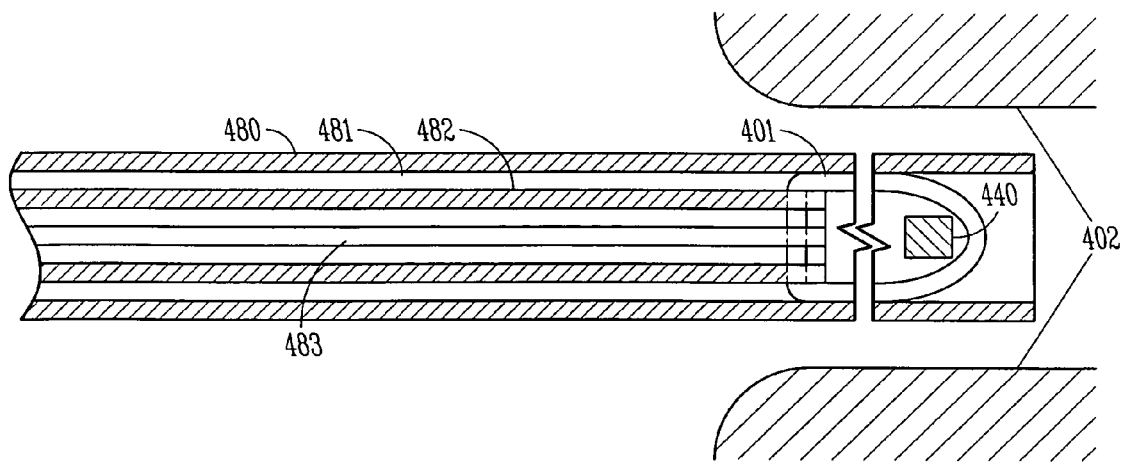
Figure 4C:
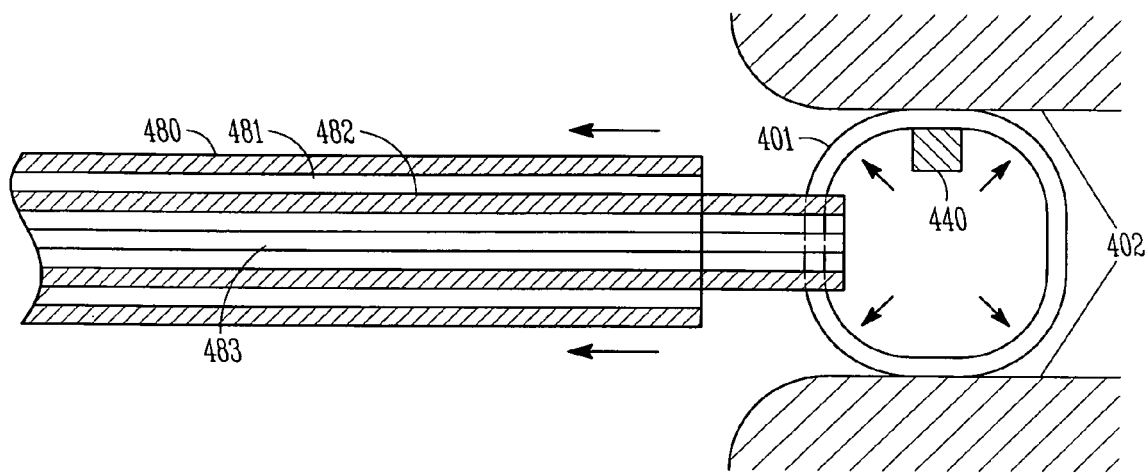
Figure 4D:
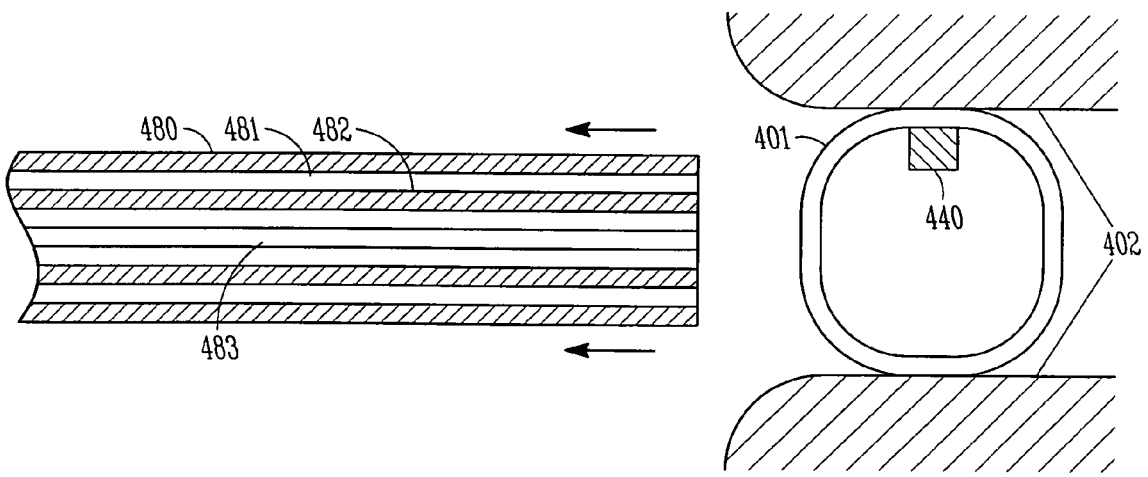

FIGS. 4A-D illustrate generally section views of an example of a system including an elongate delivery catheter 480, actuator 482, a pull wire 483, and a wireless electrostimulation electrode assembly 401 including an expandable mechanical support, and including an electrostimulation circuit 440. In FIG. 4A, the delivery catheter 480 can be steered, introduced, advanced, or otherwise navigated to a location within the heart or within a blood vessel, near a desired implant location 402, such as a blood vessel location, or some other constraining location within the heart (e.g. an atrial appendage, an aorta, a mitral valve annulus, or one or more other locations). In some examples, the delivery catheter may be introduced into the interior of a heart via a subclavian or transfemoral approach as is used for various minimally-invasive procedures such as pacemaker or defibrillator lead implantation, or such as used for percutaneous coronary interventional procedures. In the example of FIG. 4, the actuator can be attached to the electrostimulation assembly 401, such as by forcing, displacing or constraining a portion of the electrostimulation assembly 401 into a channel within the actuator 482, and holding the electrostimulation assembly 401 captive in the channel using the pull wire 483. The actuator 482, electrostimulation assembly 401, and pull wire 483 can together be translated, rotated, or pushed through the lumen 481 formed by the elongate delivery catheter 480. In FIG. 4B, the delivery catheter 480 can be further steered or advanced into the implant location 402. In an example, the actuator 482, electrostimulation assembly 401, and pull wire 483 can together be translated, rotated, or pushed out of the lumen 481 formed by the elongate delivery catheter 480, exiting the delivery catheter 480. In the example shown in FIG. 4C, the delivery catheter 480 can be retracted, leaving the actuator 482, pull wire 483, and electrostimulation assembly 401 in place at the implant location 402. In an example, one or more additional actuators or manipulators (e.g., one or more pusher tubes, push rods, push or pull wires, or one or more other actuators) can be included within the lumen 481 of the delivery catheter 480, such as to expand, rotate, move, or assemble the electrostimulation assembly 440. In the example shown in FIG. 4C, the wireless electrostimulation assembly 440 can include a portion, part or component, such as a mechanical support or body, made of a shape-memory material such as stainless steel, NiTi (nickel titanium), a polymer material, or one or more other biocompatible materials. In an example, when the electrostimulation assembly 440 is constrained by the delivery catheter 480, the electrostimulation assembly 440 can be in a folded, compressed, or collapsed configuration, and can occupy less area, length, width, or height. In an example, when the electrostimulation assembly 440 is no longer constrained by the delivery catheter 480, the electrostimulation assembly 440 can expand, unfold, open, or decompress to possess a larger area, length, width, or height, such as constrained by an implant location 402. In an example, an expansion force can be provided by the electrostimulation assembly 440, such as imparted by a shape memory material, and the expansion force can anchor the electrostimulation assembly 440 to the implant location, such as to prevent the electrostimulation assembly 440 from dislodging or moving away from the implant location 402. In certain examples, one or more of the wireless electrostimulation electrode assemblies 310, 311A-E, 313, 315, 317A-B shown in FIG. 3 can be delivered, manipulated, assembled or moved using, for example, a portion, part, or component of the system of FIGS. 4A-D.

Figure 5A:
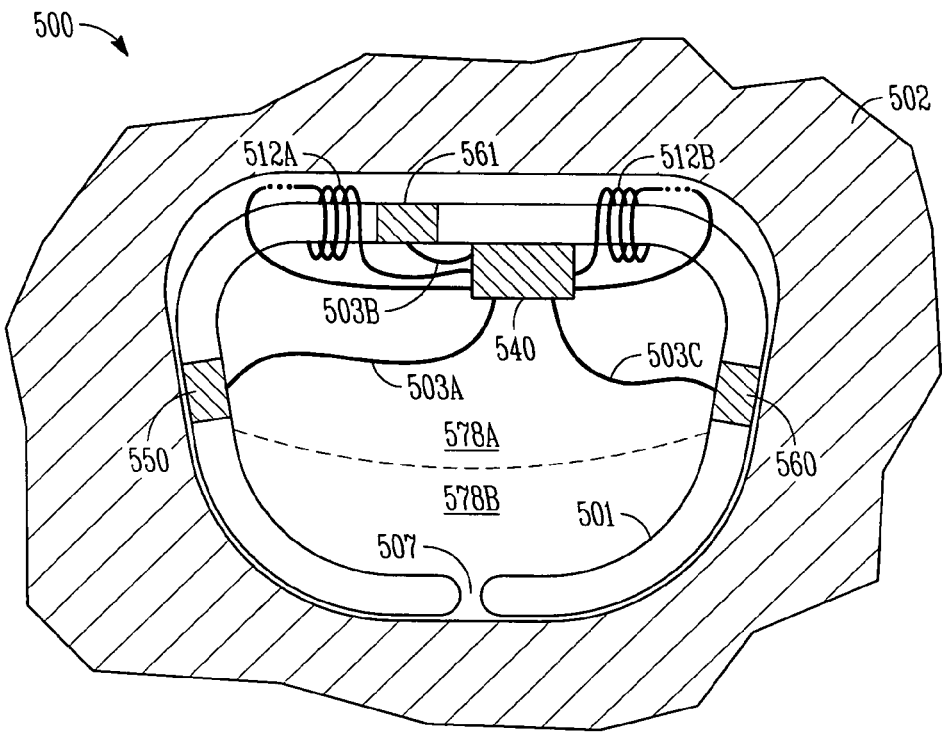
FIG. 5A-B illustrate generally examples of a wireless electrostimulation electrode assembly at a mitral valve annulus location.
Figure 5B:
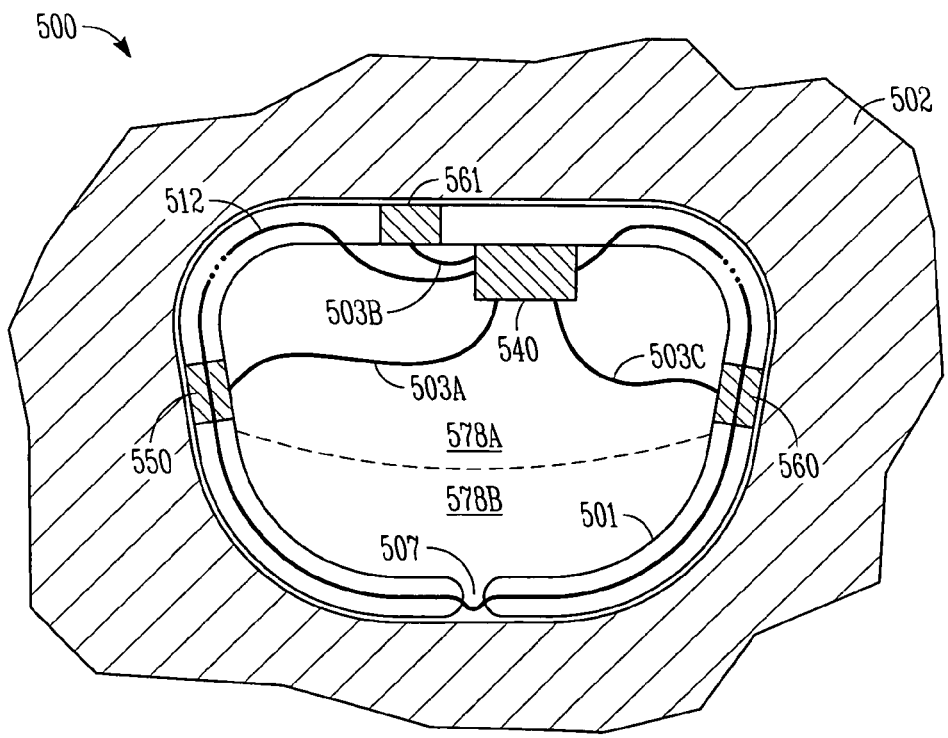

FIGS. 5A-5B illustrate generally examples of a wireless electrostimulation electrode assembly 500 at a mitral valve annulus location within the left atrium of a heart 502. An expandable mechanical support 501 can conform to and at least partially encircle a ring formed by the mitral valve annulus, such as just above the anterior and posterior leaflets 578A, 578B. A portion, part, or component of the mechanical support 501 can be made from a shape memory material to provide an expansion force to anchor the electrostimulation assembly 500 at the mitral valve location. In an example, the electrode assembly 500 of FIGS. 5A-B can be delivered, assembled, manipulated, or moved using a transluminal, intravascular, catheter-based approach such as shown in FIGS. 4A-D. In certain examples, the cross-section or shape of the expandable mechanical support 501 can include a circular cross section (e.g., including a wire shape or tubular shape, etc.), an elliptical cross section, a rectangular cross section, or one or more other shapes, such as to provide a flexible mechanical support including at least a portion configured to conform to the ring of the mitral valve annulus. In certain examples, the expandable mechanical support 501 can be fabricated using extrusion, laser cutting, stamping, molding, lithographic etching, or using one or more other techniques, methods, or processes.

Figure 6A:
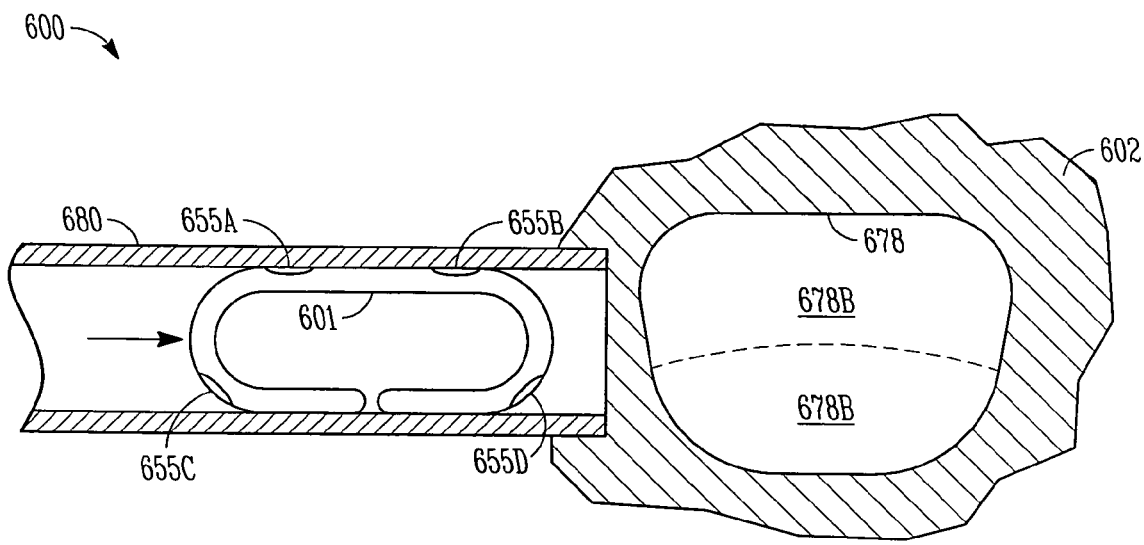
FIGS. 6A-B illustrates generally section views of an example of a system including a delivery catheter, and a wireless electrostimulation electrode assembly including an expandable mechanical support and multiple extending tines.
Figure 6B:
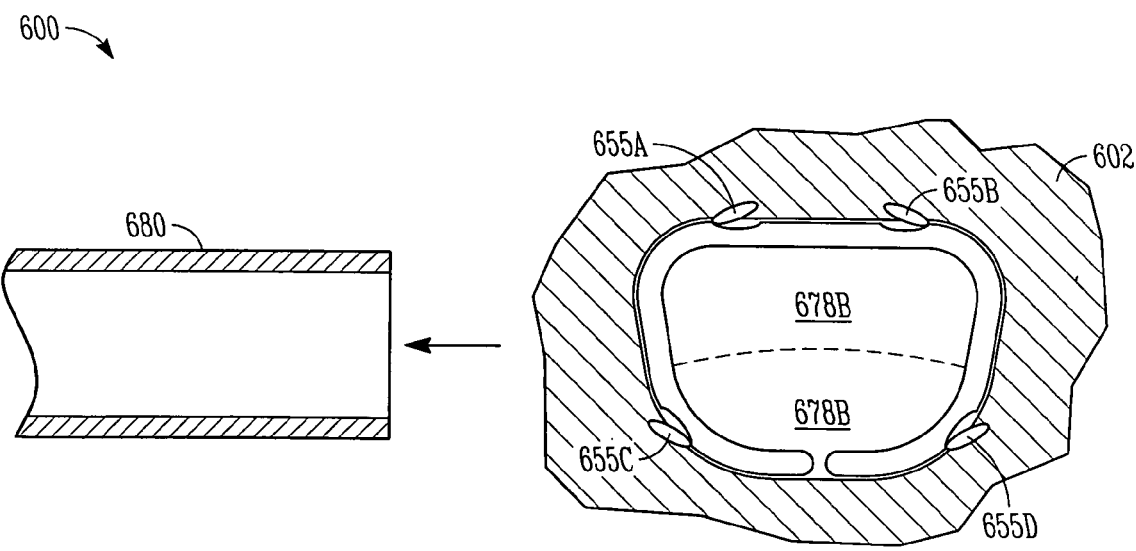

In FIGS. 5A-B, the electrode assembly 500 can include one or more electrostimulation electrodes 550, 560, 561 coupled to cardiac tissue of the heart 502. In some examples, a fibrous tissue layer at the annulus can inhibit electrostimulation or raise a threshold needed to evoke a depolarization, reducing the efficiency of the electrostimulation. In such examples, the electrostimulation electrode assembly 500 can include electrodes having a spine, a tine, a helix, a barb or one or more other features to penetrate into the fibrous layer and through to a myocardial tissue layer in order to provide electrostimulation to the myocardial tissue directly, such as shown in FIGS. 6A-B. In an example, the electrode 550 can be an anode electrode, and the electrode 560 can be a cathode electrode. In certain examples, the electrostimulation assembly 500 can include multiple cathode electrodes, such as, for example, electrodes 560-561, and a commonly shared anode, such as electrode 550. In FIGS. 5A-B, an electrostimulation circuit 540 can be coupled to electrodes 550, 560, and 561 using conductive connections 503A, 503C, and 503B, respectively. In an example, the electrostimulation assembly 540 can include one or more parts, components, or circuits such as shown in the wireless electrostimulation electrode assembly 210 of FIG. 2. In an example, the electrostimulation assembly 540 can be similar to or the same as the wireless electrostimulation electrode assembly 110 shown in FIG. 1. In the example of FIG. 5A, the electrostimulation assembly 500 can include one or more inductive pickups 512A, 512B to receive magnetically-coupled energy from a location within or outside the heart 502, such as from a controller/transmitter 220, 320 as shown in FIGS. 2-3. In an example, the one or more inductive pickups 512A, 512B can be one or more inductive coils wrapped around or on one or more sides of the mechanical support 501. In an example, the one or more inductive pickups 512A, 512B can be configured to receive or transmit magnetic fields in a spatially orthogonal manner to minimize sensitivity to a particular orientation of the electrostimulation assembly 500, such as when the electrostimulation assembly transmits or receives magnetically-coupled energy.

In certain examples, such as the examples of FIGS. 5A-B, the expandable mechanical support 501 need not completely encircle the ring formed by the annulus of the mitral valve. For example, patients can have annulus shapes and sizes that can vary, such as for an individual patient over time, or between different patients. In certain examples, such as shown in FIGS. 5A-B, a gap 507 along the circumference of the expandable mechanical support 501 can allow the expandable mechanical support 501 to flex or bend to occupy a larger or smaller ring size, and to conform to the shape of the ring formed by the mitral valve annulus. In certain examples, diagnostic imaging such CT, PET, fluoroscopic imaging, ultrasonic imaging, or one or more other forms of imaging can be used to non-invasively assess a size of the ring formed by the mitral valve annulus, and a corresponding expandable mechanical support 501 can be selected for a particular patient at a particular time (such as shortly after imaging, the support 501 sized and shaped to fit the particular patient). In certain examples, a wireless electrostimulation electrode assembly 500 such as shown in FIGS. 5A-B can be a portion, part or component of a prosthetic implant for mitral valve reconstruction, or such an electrostimulation assembly can be implanted during mitral valve annuloplasty procedure.

In the example of FIG. 5B, one or more inductive pickups 512 can include one or more turns of wire, for example, included on one or more faces of the electrostimulation assembly 500, such as, for example, to receive or transmit magnetic energy over a cross sectional area including a substantial portion of a cross section of the mitral valve annulus. In certain examples, the gap 507 can be crossed by a flexible portion of the inductive pickup 512, such as, for example, to better allow the inductive pickup and the mechanical support 501 to adjust or conform to the anatomy of the mitral valve annulus of the particular patient.

FIGS. 6A-B illustrates generally section views of an example of a system 600 including a delivery catheter 680, and a wireless electrostimulation electrode assembly 601 including an expandable mechanical support and one or more extending tines 655A-D. In an example, a delivery system similar to FIG. 5 can be used to move, manipulate, assemble, or rotate the electrostimulation assembly 601 at or near the mitral valve annulus 678 above the anterior and posterior leaflets 678A, 678B in the left atrium of a heart 602. In FIG. 6A, the one or more extending tines 655A-D can be in a collapsed, folded, or retracted position such that the electrostimulation assembly 601 can be freely moved, translated, or rotated within the delivery catheter 680. In FIG. 6B, when the delivery catheter 680 is retracted, the one or more extending tines 655A-D can be extended into tissue at or near the mitral valve annulus 678 to anchor the electrostimulation assembly 601 to the annulus 678 within the heart. In an example, the extending tines can include a portion, part, or component made of a shape memory material, such that when the delivery catheter 680 is retracted, the extending tines can automatically extend, unfold, pop out of a cavity, or otherwise deploy into cardiac tissue such as to anchor the electrostimulation assembly 601. In an example, the one or more extending tines 655A-D can provide one or more electrostimulation sites penetrating through a fibrous layer at the mitral valve annulus 678. In an example, one or more of the extending tines 655A-D can be an electrode coupled to an electrostimulation circuit included as a portion, part or component of the wireless electrostimulation electrode assembly 601. In certain examples, one or more of the wireless electrostimulation electrode assemblies 310, 311A-E, 313, 315, 317A-B shown in FIG. 3 can include a spine, a tine, a helix, a barb or one or more other features to penetrate into cardiac tissue, such as the extending tines of FIGS. 6A-6B, such as to anchor the one or more wireless electrostimulation electrode assemblies, or to penetrate into the myocardium from within a heart or within a blood vessel.

Figure 7:
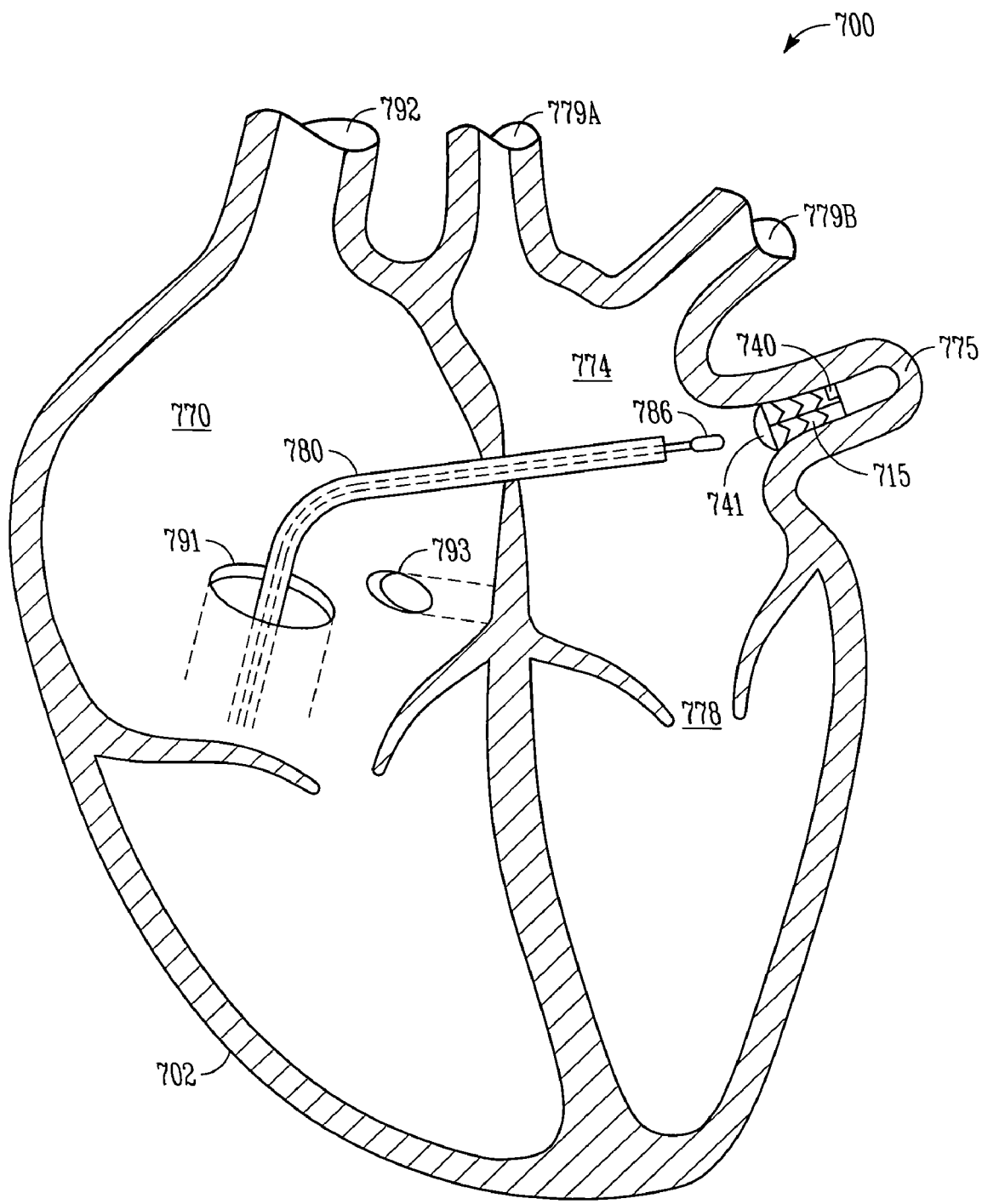
FIG. 7 illustrates generally an example of a system including a delivery catheter, actuator, inflation balloon, and wireless electrostimulation electrode assembly.

FIG. 7 illustrates generally an example of a system 700 including a delivery catheter 780, an inflation balloon 786, and wireless electrostimulation electrode assembly 715 located at a left atrial appendage 775. In an example, a transfemoral approach can be used to guide the delivery catheter through the vasculature to the inferior vena cava 791, into a right atrium of a heart 702, and then through the atrial septal region, such as through the fossa ovalis, allowing the delivery catheter to enter the left atrium 774 of the heart. In certain examples, such an approach can be used to deliver one or more wireless electrostimulation electrode assemblies, such as one or more of the wireless electrostimulation electrode assemblies 310, 311A-E, 313, 315, 317A-B shown in FIG. 3. A superior vena cava 792 can be used as a route into the right atrium 770 for the delivery catheter 780 in addition to or instead of the inferior vena cava 791, (e.g., as used for implant of one or more conductive pacemaker lead systems). In the example of FIG. 7, the wireless electrostimulation electrode assembly 715 can include a stent-like expandable mechanical support, and an electrostimulation circuit 740 coupled to one or more electrostimulation electrodes, or to the expandable mechanical support. In certain examples, the wireless electrostimulation electrode assembly 715 or one or more of the stent-like wireless electrostimulation electrode assemblies 311A-E can include an expandable mechanical support including a portion, part or component made of a shape memory material, and the one or more electrode assemblies can self expand when the delivery catheter 780 is retracted or removed. In the example of FIG. 7, an inflation balloon can be advanced to a region inside the one more stent-like wireless electrode assemblies, and the balloon can be inflated to expand at least some of the wireless electrostimulation electrode assembly to anchor the assembly at the implant location. In FIG. 7, the electrostimulation assembly 715 can include a screen, mesh or other semi-permeable or impermeable layer 741 to prevent a blood clot or other debris within the left atrial appendage 775 from escaping into the rest of the circulatory system. In this example, layer 741 can include a hole or other passage to allow the inflation balloon 786 to pass through the screen when the balloon 786 is deflated, while still allowing the balloon 786 to expand the mechanical support of the electrode assembly 715. In an example, the layer 741 can include a surface treatment or antithrombogenic compound to inhibit or reduce blood clot formation, or to enhance tissue growth around or on top of the layer 741. In an example, an endothelial layer of tissue can grow around, throughout, or on top of the layer 741 completely occluding or blocking the opening to the left atrial appendage 775.

In certain examples, the wireless electrostimulation electrode assembly 715 or one or more of the stent-like wireless electrostimulation electrode assemblies 311A-E can include one or more inductive pickups (such as one or more wire coils) separate from the expandable mechanical structure, but attached to the expandable mechanical structure. The one or more inductive pickups can be collapsed, folded, or compressed to allow the electrode assembly to pass through a lumen of the delivery catheter 780, and can be expanded by, for example, a self-expanding mechanical support, or by an inflation balloon 786 passed through the lumen of the delivery catheter to the implant location. The delivery catheter need not make a sharp curvature as shown in FIG. 7, such as when a suitable trans-septal path from the right atrium 770 into the left atrium 774 can be found near or above the inferior vena cava 791, such as near or through the fossa ovalis. In certain examples, the delivery catheter can be very small, such as 2Fr-3Fr, for example, to minimize trauma associated with crossing the atrial septum to reach the left atrium. In certain examples, the delivery system including the delivery catheter 780 and the inflation balloon 786 can be used to delivery, expand or anchor one or more other wireless electrostimulation electrode assemblies to one or more other locations within the heart, from within the heart, such as one or more right or left pulmonary veins, 779A, 779B, the superior vena cava 792, the inferior vena cava 791, the coronary sinus 793, or one or more other locations.

Figure 8:
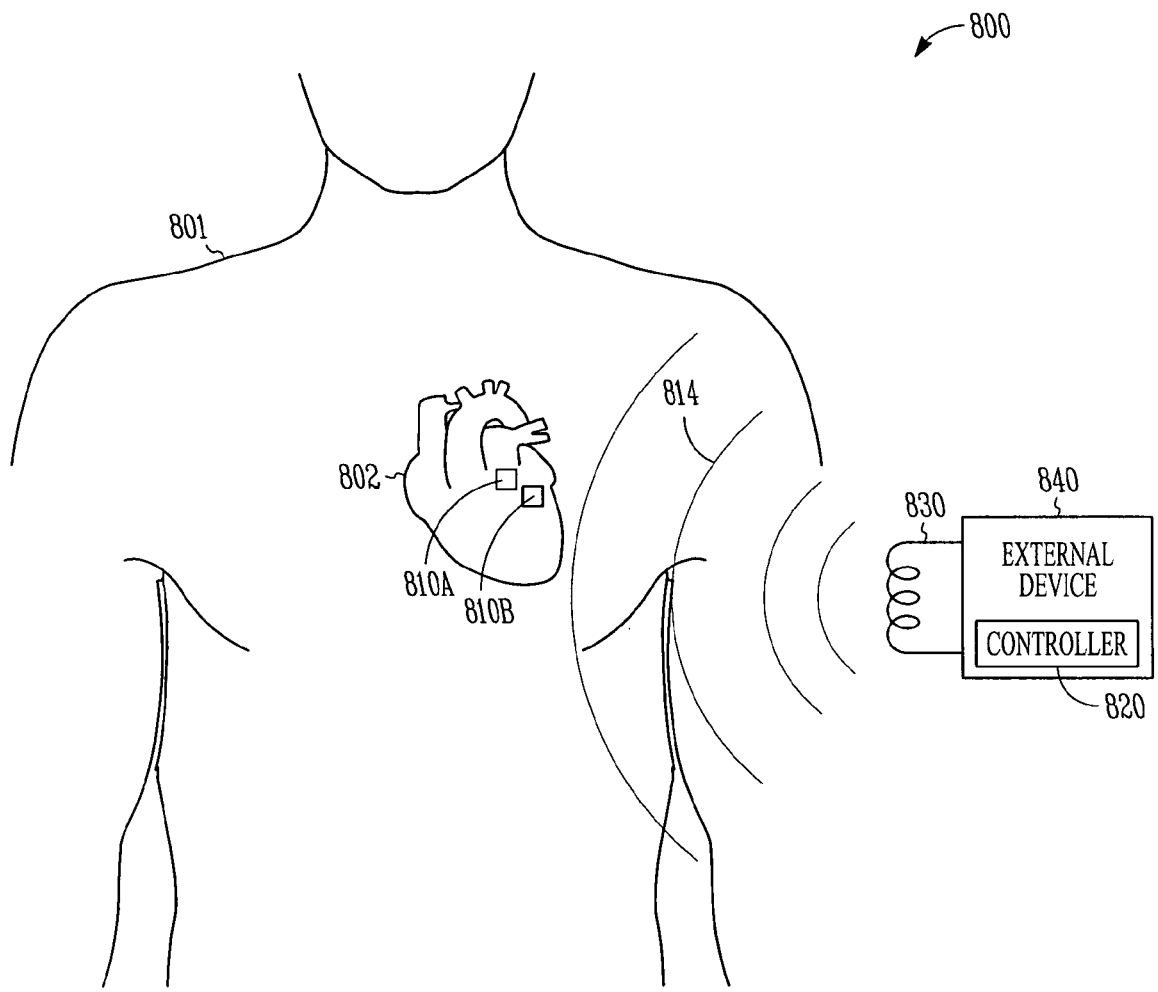
FIG. 8 illustrates generally an example of an apparatus including an external device including a transmitter and a controller, and multiple wireless electrostimulation electrode assemblies.

FIG. 8 illustrates generally an example of an apparatus 800 including an external device 840. In certain examples, the external device can include a transmitter 830 and a controller 820, and the apparatus 800 can include one or more wireless electrostimulation electrode assemblies, such as a first wireless electrostimulation electrode assembly 810A, or a second wireless electrostimulation electrode assembly 810B. In certain examples, the one or more wireless electrostimulation electrode assemblies can be located in one or more blood vessels near a heart 802, or endocardially in the heart 802 itself. In certain examples, the external device 840 can include a part, portion or component similar to the controller/transmitter 220 of FIG. 2. In certain examples, the external device 840 can include a pocket-sized assembly such as a personal digital assistant, a hand-held patient activator (e.g., to provide a patient 801 with one or more indicators or controls to assess the patient's status, or to control one or more therapy parameters), an external physician programmer for an implantable cardiac rhythm management system, a hospital bed or one or more other forms of furniture, or one or more other external devices. In certain examples, the apparatus 800 can be used as a portion, part or component of, or in addition to a conventional cardiac rhythm management system (e.g., the conventional cardiac rhythm management system using conductive lead assemblies attached to a subcutaneous pulse-generator).

Figure 9:
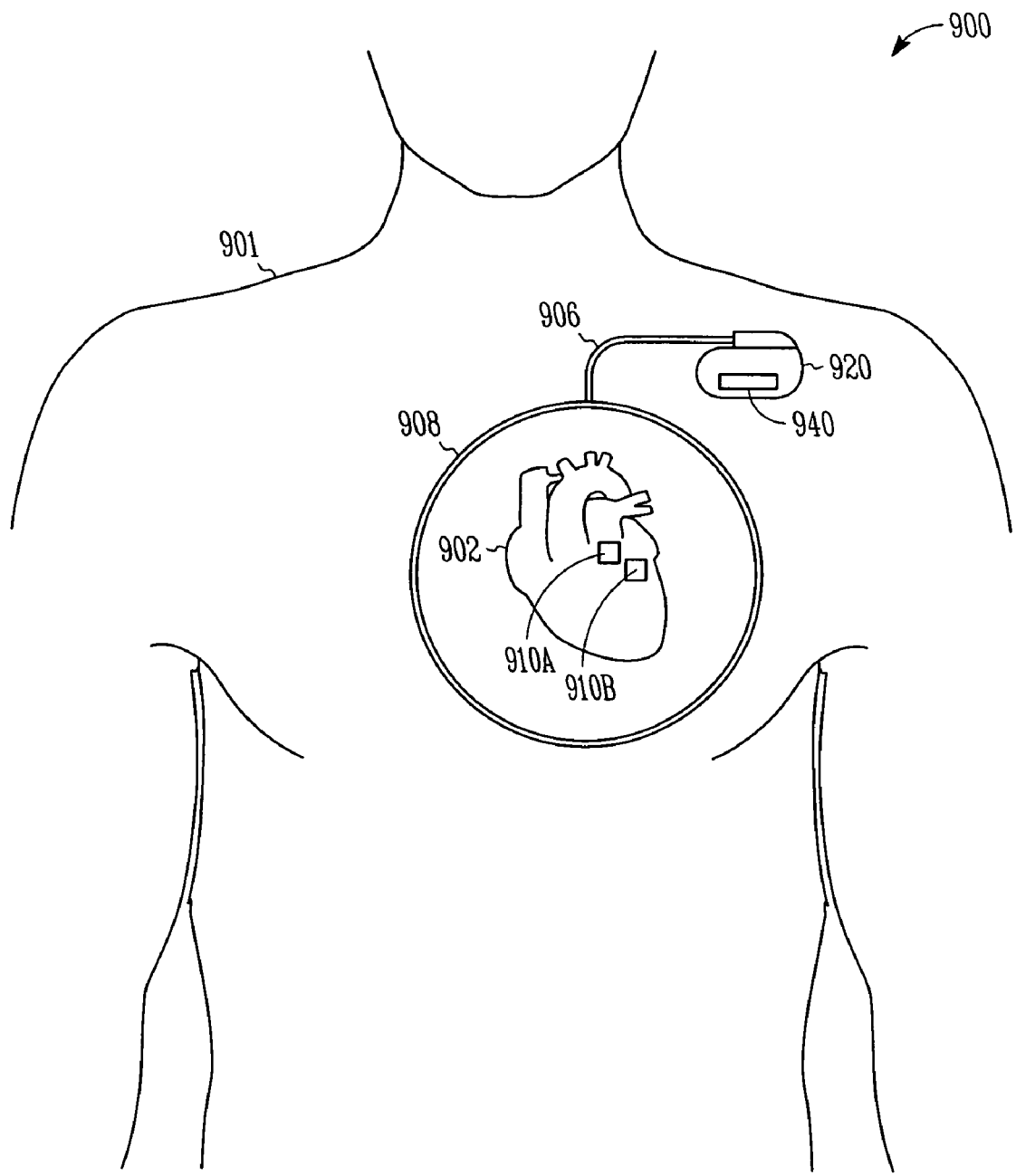
FIG. 9 illustrates generally an example of an apparatus including an implantable device including a subcutaneous transmitter and a controller, and multiple wireless electrostimulation electrode assemblies.

FIG. 9 illustrates generally an example of an apparatus 900 including an implantable device 920, such as a cardiac rhythm management pulse generator assembly, including a subcutaneous transmitter and a controller 940, and one or more wireless electrostimulation electrode assemblies, such as a first wireless electrostimulation electrode assembly 910A, or a second wireless electrostimulation electrode assembly 910B located in a patient 901 within one or more blood vessels near a heart 902, or endocardially in the heart 902 itself. In the example of FIG. 8, a lead 906 can be used to conductively couple an inductive antenna 908 to the implantable device 920. In an example, the lead 906 can be constructed similarly to a conventional implantable lead, such as by using one or more coiled concentric conductors encapsulated by a flexible biocompatible insulating layer such as silicone, or one or more other materials or constructions. In an example, the lead 906 can be electrically connected to the implantable device 920 using a header similar to a header used by a conventional cardiac rhythm management device, in addition to or instead of other leads. In certain examples, the implantable device 920 can include a pacemaker, a cardiac resynchronization therapy device, an implantable cardioverter defibrillator, a neural stimulation device, or one or more other active implantable medical devices.

Figure 10:
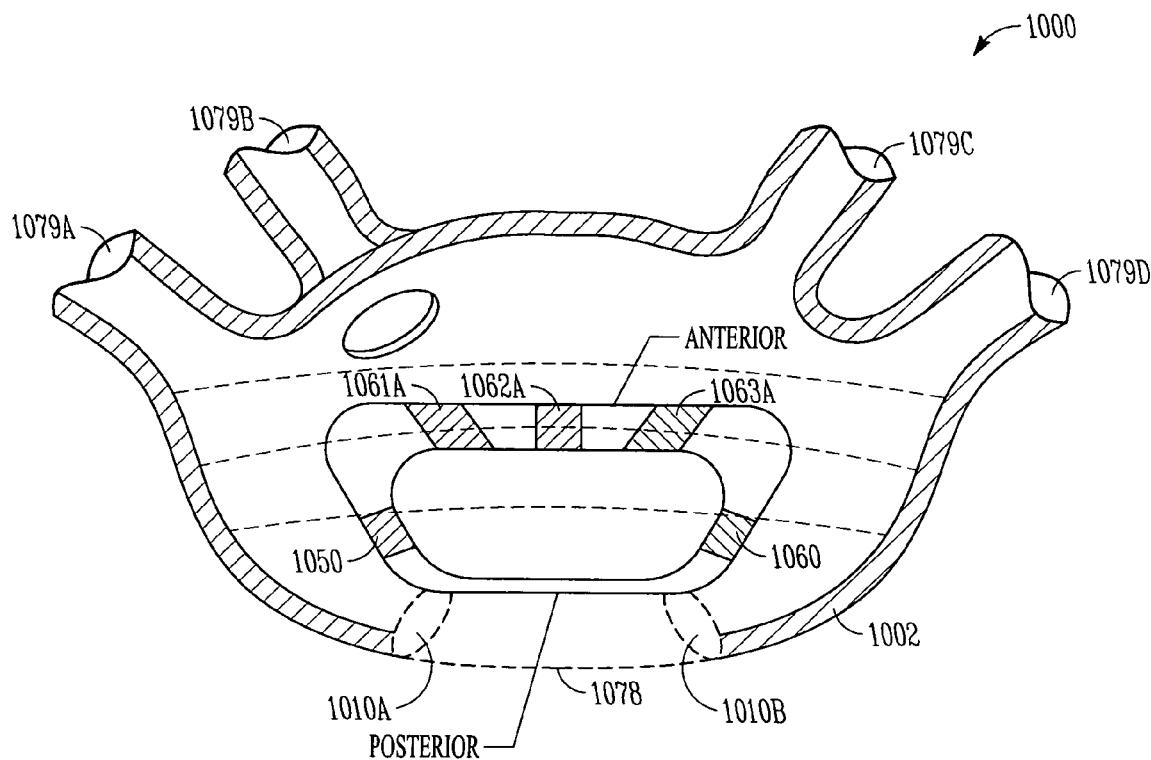
FIG. 10 illustrates generally an example of a wireless electrostimulation electrode assembly including a loop-shaped mechanical support coupled to one or more mechanical struts, the mechanical struts at least partially encircling and supported by a mitral valve annulus.

FIG. 10 illustrates generally an example of a wireless electrostimulation electrode assembly 1000 including a loop-shaped mechanical support 1001 coupled to one or more mechanical struts, such as a first strut 1010A, or a second strut 1010B, the struts at least partially encircling and supported by a mitral valve 1078 annulus. In the example of FIG. 10, the electrostimulation assembly 1000 can be supported at least partially at the mitral valve annulus, such as at a wedge formed between a left atrial wall and a posterior region of the annulus, and the assembly 1000 can wrap around an interior of the left atrium at least partially in contact with an anterior region of endocardium opposite the posterior region of the annulus, such as, for example, below a plane formed by the bottom of the pulmonary veins, such as a first and second right pulmonary vein, 1079A, 1079B, and a first and second left pulmonary vein 1079C, 1079D. In the example of FIG. 10, the electrostimulation assembly 1000 can include one or more electrodes around the circumference of the loop-shaped mechanical support 1001, such as a first electrode 1050, a second electrode 1060, a third electrode 1061A, a fourth electrode 1062A, and a fifth electrode 1063A. In some examples, the mechanical support 1001 can be conductive, and can carry an electrostimulation current to one or more of the first, second, third, fourth, or fifth electrodes 1050, 1060, 1061A, 1062A, or 1063A. In certain examples, one or more electrostimulation electrodes, such as one or more of the first, second, third, fourth, or fifth electrodes 1050, 1060, 1061A, 1062A, or 1063A, can be formed by providing one or more openings in an insulating layer covering, coating, encapsulating, or surrounding the mechanical support 1001. In certain examples, the electrode used for electrostimulation can be selected by a controller including an arrhythmia detector in order to deliver one or more coordinated electrostimulations using a selected group or combination of electrodes in order to regulate, terminate, or control an arrhythmia. In certain examples, one or more cathode electrodes can be used, and a total surface area of the one or more cathode electrodes can be, for example, substantially equivalent to a surface area of an anode electrode to provide a specified current density at the one or more cathode electrodes, such as, for example, to provide reliable electrostimulation at the one or more cathode electrode locations. In an example, the loop-shaped mechanical support 1001 can be folded, compressed, or collapsed, such as for delivery via a percutaneous, transluminal route through one or more blood vessels using a delivery catheter, such as shown in FIGS. 4A-D. In an example, the electrostimulation assembly 1000 can include one or more components, circuits, or portions of the wireless electrostimulation electrode assembly 210 shown in FIG. 2. In an example, the first or second mechanical struts 1010A, 1010B can omitted and the loop-shaped mechanical support 1001 can be expandable, and can be directly supported at least partially by the ring formed by the mitral valve annulus 1078. In certain examples, the loop shaped mechanical support 1001 can be in contact with cardiac tissue along its entire circumference, such as, for example, to encourage growth of a protective layer of tissue around the mechanical support 1001. In an example, growth of a protective layer of tissue at least partially around, throughout, or surrounding the support 1001 can reduce a risk of forming blood clot, as compared to having one or more portions of the support 1001 exposed to a blood pool in the left atrium.

Figure 11:
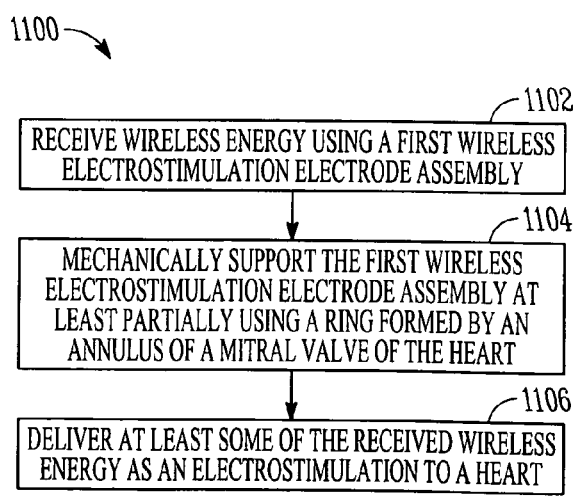
FIG. 11 illustrates generally an example of a method including receiving wireless energy and delivering at least a portion of the received wireless energy as an electrostimulation to a heart.

FIG. 11 illustrates generally an example of a method 1100 including receiving wireless energy using a first wireless electrostimulation electrode assembly at 1102, mechanically supporting the first wireless electrostimulation electrode assembly at least partially using a ring formed by an annulus of a mitral valve of a heart at 1104, and delivering at least some of the received wireless energy as an electrostimulation to a heart at 1106. In certain examples, the first wireless electrostimulation electrode assembly can be similar to or the same as the electrostimulation assembly 110 shown in FIG. 1, the electrostimulation assembly 500 shown in FIG. 5, the electrostimulation assembly 601 shown in FIGS. 6A-B, the electrostimulation assembly 1000 shown in FIG. 10, or one or more other electrostimulation assemblies. In certain examples, the first wireless electrostimulation electrode assembly can receive magnetically-coupled energy and deliver at least some of the received magnetically-coupled energy as an electrostimulation to the heart using one or more circuits, components or devices such as shown in the electrostimulation assembly 210 of FIG. 2.

Figure 12:
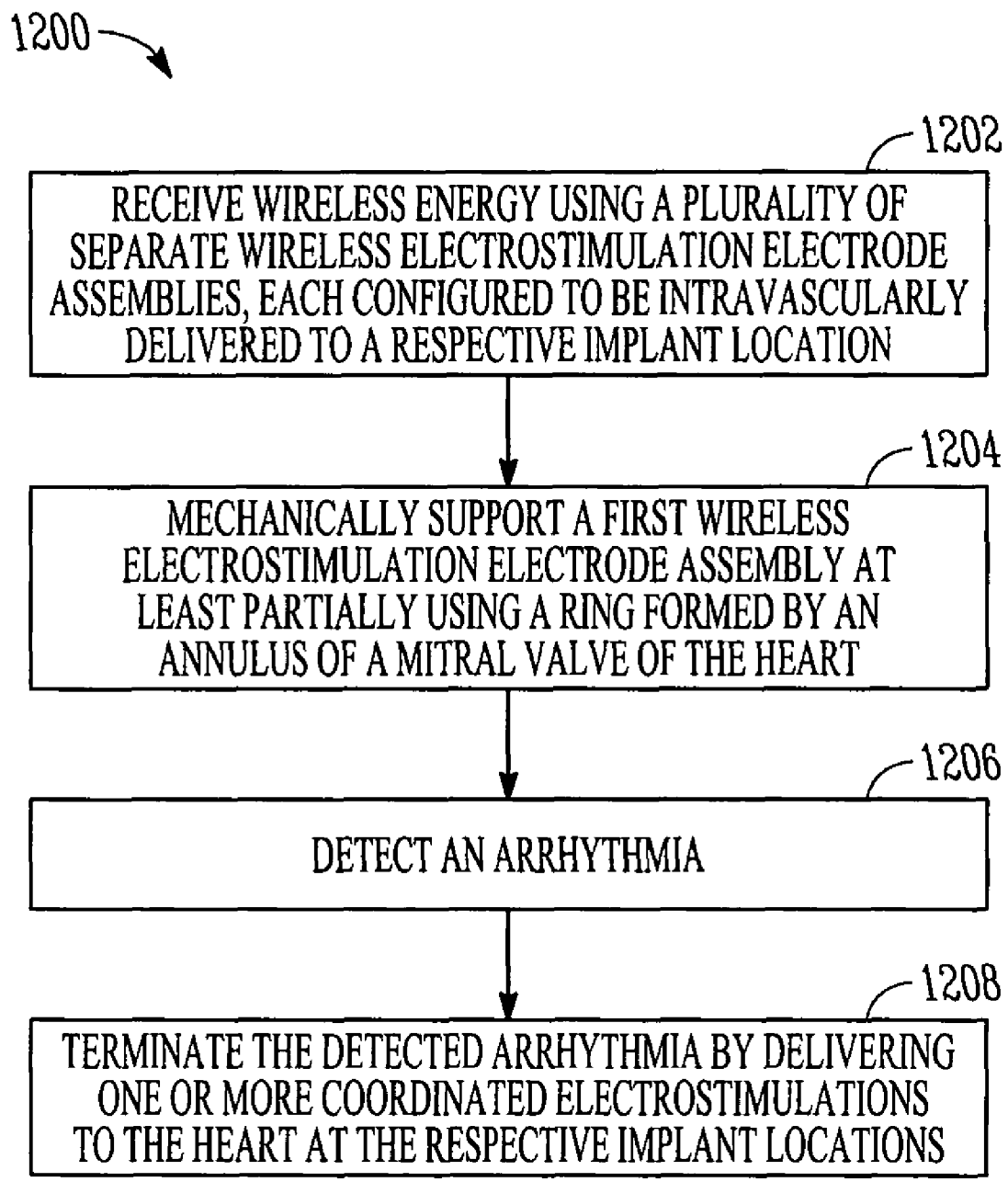
FIG. 12 illustrates generally an example of a method including receiving wireless energy, detecting an arrhythmia, and delivering at least a portion of the received wireless energy as an electrostimulation to a heart in order to terminate the arrhythmia.

FIG. 12 illustrates generally an example of a method 1200 including receiving wireless energy using a plurality of separate wireless electrostimulation electrode assemblies each configured to be intravascularly delivered to a respective implant location at 1202, mechanically supporting a first wireless electrostimulation electrode assembly at least partially using a ring formed by an annulus of a mitral valve of a heart at 1204, detecting an arrhythmia at 1206, and terminating the detected arrhythmia by delivering one or more coordinated electrostimulations to the heart at the respective implant locations at 1208. In certain examples, the first wireless electrostimulation electrode assembly can be similar to or the same as the electrostimulation assembly 110 shown in FIG. 1, the electrostimulation assembly 500 shown in FIG. 5, the electrostimulation assembly 601 shown in FIGS. 6A-B, the electrostimulation assembly 1000 shown in FIG. 10, or one or more other electrostimulation assemblies. In certain examples, one or more of the plurality of wireless electrostimulation electrode assemblies can be similar to one or more of the electrostimulation assemblies 310, 311A-E, 313, 315, 317A-B shown in FIG. 3.

In certain examples, one or more of the plurality of wireless electrostimulation electrode assemblies can receive magnetically-coupled energy and deliver at least some of the received magnetically-coupled energy to the respective implant locations using one or more circuits, components or devices such as shown in the electrostimulation assembly 210 of FIG. 2.

Figure 13A:
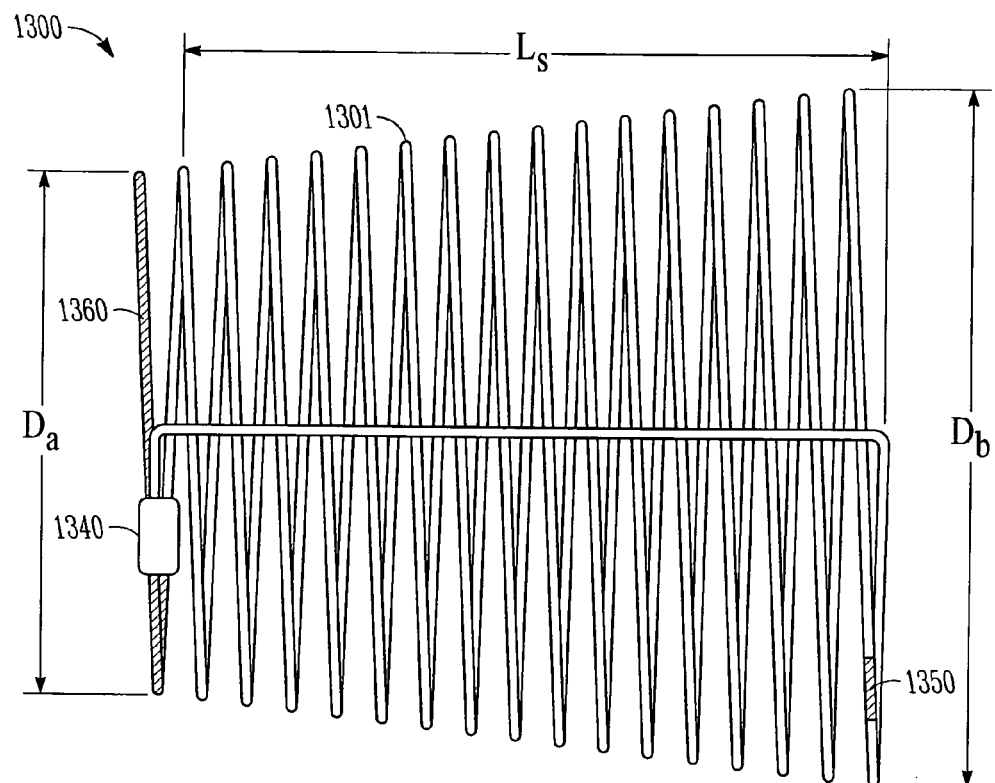
FIGS. 13A-B illustrate generally examples of a stent-like wireless electrostimulation electrode assembly.
Figure 13B:
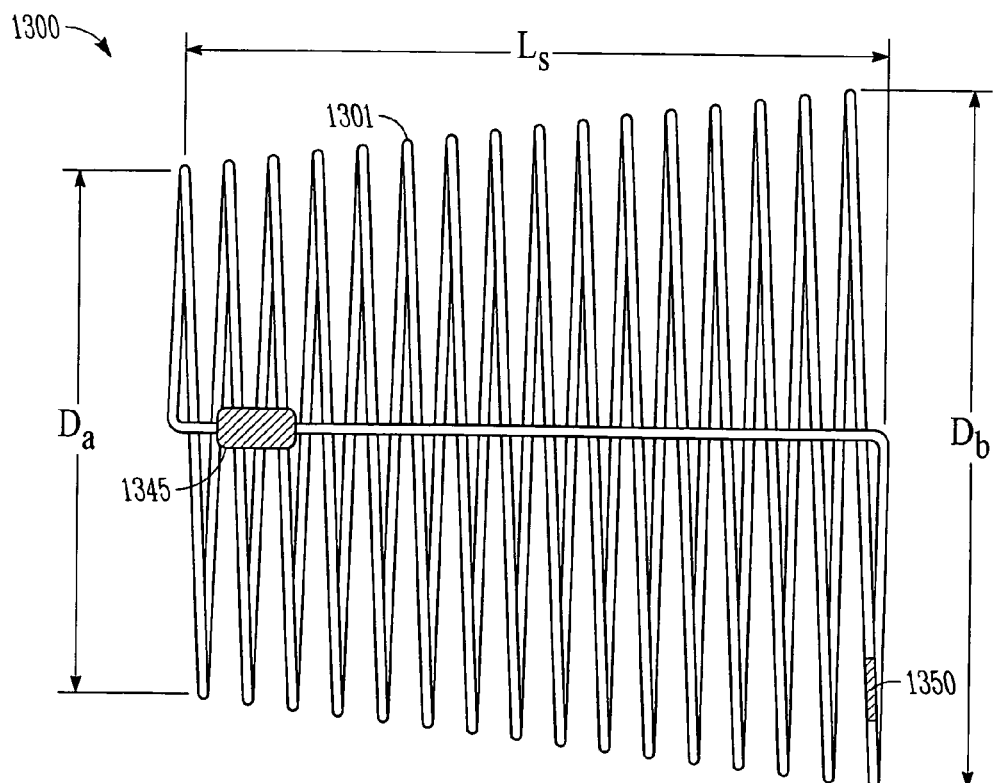

FIGS. 13A-B illustrate generally examples of a stent-like wireless electrostimulation electrode assembly 1300, such as, for example, one or more of the wireless electrostimulation electrode assemblies 311A-E shown in FIG. 3. In FIGS. 13A-B, a coiled strut 1301 can provide a mechanical support for the electrostimulation assembly 1300. In certain examples, the coiled strut 1301 can be compressed, flattened, folded, or formed into one or more wire strands, and passed through a lumen formed by an elongate delivery catheter, similar to the examples of FIGS. 4A-D, and FIG. 7. In these examples, when compressed, flattened, folded, or formed into one or more wire strands, the cross section of the electrostimulation assembly 1300 can be small enough for the electrostimulation assembly 1300 to be intravascularly delivered through one or more blood vessels to an implant location, and such an intravascular delivery can include a route through one or more heart chambers, such as, for example, to gain access to one or more pulmonary veins. In certain examples, the coiled strut 1301 can self-expand, such as, for example, to decompress, open, unfold, forming a tapered coil, such as shown in FIGS. 13A-B, after the electrostimulation assembly 1300 is delivered to the implant location. In certain examples, a portion, part or component of the coiled strut 1301 can be made of one or more conductive materials, such as, for example, an elongated tube of shape-memory material partially or completely enclosing a conductive core. In an example, the elongated tube of shape-memory material can be a nickel titanium compound or alloy, such as Nitinol, and the conductive core can be silver. In an example, the core can be the shape-memory material, such as the nickel titanium compound or alloy, and the elongated tube can be highly conductive, such as platinum, or platinum-iridium oxide. In an illustrative example, an outer diameter of the elongated tube of shape-memory material can be less than 0.008 inches, to greater than 0.012 inches. In certain examples, the coiled strut 1301 can be both a mechanical support and an inductive receiver coil, such as, for example, to receive wirelessly-coupled energy from a separate transmitter coil. In the example of FIG. 13A, one or both ends of the coiled strut can be conductively coupled to an electrostimulation circuit 1340. In certain examples, the electrostimulation circuit 1340 can include one or more parts, components or portions of the wireless electrostimulation electrode assembly 210 shown in FIG. 2. In the example of FIG. 13A, the coiled strut, or the electrostimulation circuit 1340, can be coupled to one or more cathode electrodes 1350 located proximally to the interior of a heart chamber, such as nearby or contacting a myocardial muscle sleeve within one or more blood vessels entering or exiting a heart chamber. In the example of FIG. 13A, the electrostimulation circuit 1340 can be conductively coupled to one or more anode electrodes 1360 located distally to the interior of the heart chamber. In certain examples, the one or more anode or cathode electrodes 1360, 1350 can be a part, portion, or component of the coiled strut 1301, such as, for example, one or more non-insulated portions of the strut 1301. In certain examples, the one or more anode or cathode electrodes 1360, 1350 can include an exposed platinum portion, a platinum-iridium oxide portion, or one or more other conductive biocompatible materials to be placed in contact with tissue or near tissue. In an example, the electrostimulation circuit 1340 can include a rectifier electrically connected to the coiled strut 1301, and one or more of a tuning capacitor or an electrostimulation waveform shaping capacitor conductively coupled in series or parallel to the rectifier and to one or more of the electrostimulation electrodes 1360, 1350, such as, for example, to provide a specified electrostimulation waveform when the one or more anode or cathode electrodes 1360, 1350 are in contact with tissue. In this example, the electrostimulation circuit can be very compact, such as about 0.020 inches by 0.030 inches, and 0.010 inches thick. In an example, the one or more electrostimulation electrodes 1360, 1350 can provide the specified electrostimulation waveform when the electrostimulation assembly 1300 receives magnetically coupled energy containing a specified range of frequencies. In the example of FIG. 13B, the electrostimulation circuit 1340 and the one or more anode electrodes 1360 can be included in a wall electrode 1345. In certain examples, the wall electrode 1345 of FIG. 13B can be an anode electrode, in addition to or instead of the one or more anode electrodes 1360, such as shown in FIG. 13A. In an example, circuitry included as a portion, part, or component of the wall electrode 1345 can be similar to or the same as the electrostimulation circuit 1340, such as shown in FIG. 13A. In an example, at least a portion of the wall electrode 1345 can be platinum, platinum-iridium oxide, or one or more other conductive biocompatible materials to be placed in contact with tissue or near tissue. In certain examples, the coiled strut 1301 can be used as an inductive receiver coil separate from, and attached to, a mechanical support, such as an expandable stent body. In such examples, the mechanical support can be selected for reliable anchoring of the electrostimulation assembly 1300 at the implant location, and the separate coiled strut 1301 can be selected to provide reliable inductive receiving or transmission of magnetic energy. In certain examples, a wireless electrostimulation electrode assembly 1300 can be located in a specified pulmonary vein, and one or more other electrostimulation assemblies can be located endocardially, or within one or more other blood vessels, and can be connected by one or more small leads to the wireless electrostimulation electrode assembly 1300 located in the specified pulmonary vein, without requiring the one or more small leads to exit the left atrium or the left ventricle. In these examples, the one or more small leads can be located against an endocardial wall, such as, for example, to encourage growth of a protective endothelial layer around the one or more small leads, such as for reducing a risk of a thrombus forming.

In an illustrative example, an experimental prototype can be constructed to predict an efficiency of a stent-like wireless electrostimulation electrode assembly, such as the electrostimulation assembly 1300 shown in FIGS. 13A-B. In this illustrative example, the electrostimulation assembly 1300 can be sized and shaped to be implanted in a pulmonary vein, such as, for example, one or more of the pulmonary veins 1079A-D shown in FIG. 10. In this example, the pulmonary vein can be conical, and the electrostimulation assembly 1300 can be tapered such as shown in FIGS. 13A-B, for example, such as to better conform to the conical anatomy of the pulmonary vein. A transmitter, for example, similar to the controller/transmitter 220 shown in FIG. 2 can have a transmitter coil represented by the following electrical parameters:

Diameter=D=40 millimeters
Number of Turns=N=7
Coil Resistance R=5.5 Ohms
Relative Magnetic Permeability=Air=$\mu$=1
Coil Self Inductance=L=6.3 microHenry
Coil Tuning Capacitance=C=0.001 microFarad @2.0 megaHertz resonance.

In this illustrative example, a receiver coil, such as coil 1301, included as a portion, part or component of the wireless electrostimulation electrode assembly 1300, can be represented by the following electrical parameters:

Avg. Stent Diameter=$D_1$=17.5 millimeters
Stent Length=$L_s$=20 millimeters
Number of Turns=$N_1$=16
Coil Resistance $R_1$=1.6 Ohms
Relative Magnetic Permeability=Air=$\mu$=1
Coil Self Inductance=$L_1$=3.5 microHenry
Coil Tuning Capacitance=$C_1$=0.0017 microFarad @2.0 megaHertz resonance.

In this illustrative example, the stent diameter, $D_1$, can be selected to approximate a taper in a diameter of the pulmonary vein (or one or more other veins), such as from the first diameter, $D_a$=15 millimeters, to the second diameter, $D_b$=20 millimeters, over the first 20 millimeters of the vein, corresponding to the stent length, $L_s$=20 mm. In this illustrative example, "z" can represent the separation (e.g., an elevation) between the plane of the transmitter coil located elsewhere, such as in the right atrium, and the nearest edge of the receiver coil, and a coupling constant, $\kappa$, can be represented by the following equations:

$$\kappa = [\pi D_1^2 F(z)^2]/[32 D L_2] \quad (6)$$

where $$f(z) = (z+L_s)/\sqrt{(D_1/2)^2+(z+L_s)^2} - z/\sqrt{(D_1/2)^2+z^2}. \quad (7)$$

In this illustrative example, "z" can be 8 millimeters, such as to represent a separation between a nearest edge of a wireless electrostimulation electrode assembly 1300 located near the heart in the pulmonary vein and a plane formed by a transmitter coil in the right atrium, such as included as a portion, part, or component of an intravascular lead located in the right atrium. Using EQUATIONS (1) and (2) as discussed above for FIG. 2, an efficiency, $\eta$, and a peak load voltage, $|V_L|$ can be determined. The peak load voltage can represent, for example, an electrostimulation voltage across two electrostimulation electrodes connected to heart tissue, during an electrostimulation. In this illustrative example, a resistive load, $R_L$=500 Ohms, can be placed across the receiver coil contacts, such as shown in discussed in FIG. 2, and a transmit coil excitation voltage of $|V_0|$=5 Volts at 2 megaHertz can be applied to the transmitter coil. Using EQUATIONS (1) and (2), and the coupling constant, $\kappa$, of EQUATIONS (6) and (7), $|V_L|$=20 Volts when $|V_0|$=5 Volts, and $\eta$=32% when z=8 millimeters. In an illustrative example, if a cardiac rhythm management device using a tethered intravascular lead has a battery that can last 15 years providing a similar electrostimulation load voltage, then at $\eta$=10%, the wireless electrostimulation electrode assembly could be powered for 1.5 years using a subcutaneous transmitter and a similar battery to that of the tethered cardiac rhythm management device.

In certain examples, received power can diminish as the angle between the planes of the transmitter and receiver coils deviates from zero degrees (reducing the coupling constant, $\kappa$), resulting in orientation sensitivity. In certain examples, multiple transmit coils in multiple planes, and even multiple coils in a single plane, can help reduce such orientation sensitivity. Multiple receiver coils consume little additional energy in the far field of the transmitter, compared to using a single receiver coil. Thus, multiple receivers can operate near an inductive transmitter with an efficiency substantially equal to the efficiency of a single receiver. In certain examples, the inductive transmitter can be located in one or more other locations, including an esophagus, one or more bronchi, a pericardial space, a pulmonary artery, or one or more other subcutaneous or external locations. Similar to the discussion for FIG. 10, in certain examples, one or more types of medical imaging can be performed prior to or during an implantation of one or more electrostimulation assemblies 1300, such as, for example, to provide information that can be used to select an appropriate size and shape of electrostimulation assembly 1300 for a particular location, or a particular patient. In an illustrative example, one or more pulmonary veins may range from less than 10 millimeters in diameter at a distal end, to more than 25 millimeters in diameter at a proximal end near the heart, and a corresponding range of wireless electrostimulation assembly 1300 shapes and sizes can be provided to match the one or more pulmonary veins.

Figure 14:
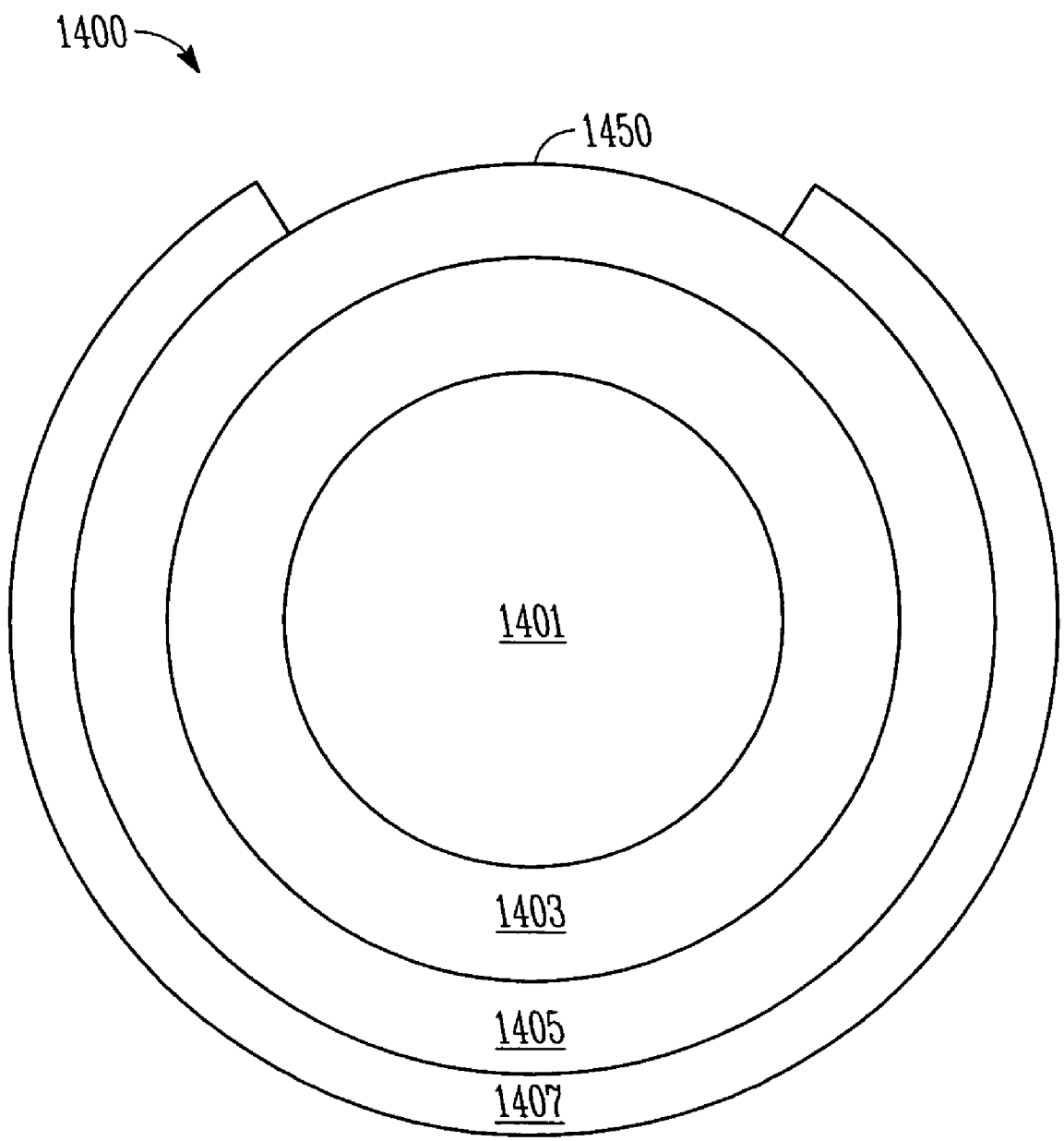
FIG. 14 illustrates generally a section view of at least a portion of a wireless electrostimulation electrode assembly.

FIG. 14 illustrates generally a section view 1400 of at least a portion of a wireless electrostimulation electrode assembly. In an illustrative example, the section view of FIG. 14 can include a cross section of a portion of a wireless electrostimulation assembly 1300, such as shown in FIG. 13. A conductive core 1401 can provide a low resistance path for received magnetic energy or energy to be delivered as an electrostimulation. The present inventors have recognized that some conductive materials can have low resistance, but can lack shape-memory or spring-like properties. The present inventors have also recognized that a tube, a coating, a plated layer, or a jacket of shape-memory material 1403 can be included in addition to the conductive core 1401, such as, for example, to provide a combined assembly 1300 including both a highly conductive portion, and a spring-like or shape-memory portion. In an example, the shape-memory material 1403 can be co-extruded along with the conductive core, or one or more other materials, such as to form a combined assembly 1300. In certain examples, the shape-memory material 1403 can provide an expansion force, such as, for example to decompress, unfold, expand, or anchor the electrostimulation assembly 1300 at an implant location. In certain examples, the electrostimulation assembly 1300 can at least partially self-decompress, self-unfold, or self-expand, such as, for example, using the expansion force of the shape-memory material 1403. In the example of FIG. 14, an electrode layer 1405 can be attached to the shape-memory material 1403, or directly to the core 1401. In certain examples, one or more portions of the electrode layer 1405 can be encased, surrounded, encapsulated, coated, or otherwise treated with an insulator 1407, such as, for example, a biocompatible material such as silicone, or one or more other materials. One or more electrodes 1450 can be provided by including one or more openings, cavities, or apertures in the insulating layer 1407, such as, for example, to expose a portion of the electrode layer 1405. In certain examples, at least a portion of the electrode layer can include platinum, platinum-iridium oxide, or one or more other conductive biocompatible materials, for example, to provide reliable electrostimulation when the electrode 1405 is in contact with tissue, or near one or more tissue sites to be electrostimulated. In certain examples, the shape-memory material 1403 need not surround the core 1401, and the core itself can be a shape memory material surrounded by one or more conductive layers, such as discussed above for FIGS. 13A-B.

ADDITIONAL EXAMPLES

In an example, one or more wireless electrostimulation electrode assemblies can condition myocardial tissue after a myocardial infarction, such as to limit, control, or prevent adverse remodeling of myocardial tissue resulting from damage caused by the infarction. In such an example, one or more coordinated electrostimulations delivered by one or more wireless electrostimulation electrode assemblies can limit tissue damage or death within or near one or more infracted tissue sites. In an example, over a longer term such as from days to months, or longer, after an infarction, one or more coordinated electrostimulations can be delivered by one or more wireless electrostimulation electrode assemblies, for example, such as to limit an increase in infracted tissue volume, or to enhance a cardiac ejection fraction. Such examples called "myocardial salvage," or "remodeling control therapy."

In certain examples, one or more stent-like wireless electrostimulation electrode assemblies, such as shown in FIGS. 3, 7, can be used in other locations within a patient, such as one or more arteries, arterioles or veins, such as to enhance perfusion (e.g., such as after a stroke in a cerebral location) or to encourage diuresis (via an implant location in a renal artery), either through modulation of one or more vascular neurological pathways (such as to evoke vasodilation or vasoconstriction), or through evoking or inhibiting a contractile response in nearby muscle tissue. In an example, one or more wireless electrostimulation assemblies can be placed in a renal artery or a renal vein, and dilation of the renal artery or vein can be evoked using the one or more wireless electrostimulation assemblies. In an example, electrostimulation by one or more wireless electrostimulation electrodes to elicit diuresis can be used to enhance perfusion around one or more blood vessels or to clear debris from within or near one or more blood vessels, such as after an ischemic event. In an example, vasodilation of pulmonary arteries can be used to control, prevent, or limit pulmonary hypertension.

In certain examples, one or more wireless electrostimulation electrode assemblies can include an antithrombogenic agent or surface treatment, such as, for example, to promote incorporation of the electrostimulation assembly into the surrounding tissue, such as a blood vessel wall. In an example, an endothelial layer can grow around, on, or throughout the electrostimulation assembly, and can protect the electrostimulation assembly, such as to reduce a risk of thrombus formation. In an example, one or more wireless electrostimulation electrode assemblies can include a roughened or porous surface treatment to enhance in-growth of surrounding tissue. In an example, sub-threshold electrostimulation can be provided (e.g., delivering an electrostimulation having an energy or voltage below a threshold where muscle contraction can be elicited). In an example, such sub-threshold electrostimulation might enhance tissue ingrowth or reduce or eliminate redosing of a blood vessel where the electrostimulation electrode is located (e.g., to prevent or reduce restenosis).

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:
1. An apparatus, comprising:
a first wireless electrostimulation electrode assembly comprising:
an electrostimulation circuit;
a wireless receiver configured to receive wireless energy and configured to provide at least some of the received wireless energy to the electrostimulation circuit;
a first expandable support mechanically coupled to the electrostimulation circuit and the wireless receiver and configured to support the first wireless electro- stimulation electrode assembly at least partially using a ring formed by an annulus of a mitral valve of the heart; and wherein the electrostimulation circuit is configured to deliver at least some of the received wireless energy as an electrostimulation to the heart;

wherein the first wireless electrostimulation electrode assembly is configured to be intravascularly delivered to an implant location within a chamber of the heart at the annulus of the mitral valve of the heart; and wherein the first wireless electrostimulation electrode assembly is configured to fit entirely within the heart.

2. The apparatus of claim 1, wherein the wireless energy includes magnetically-coupled energy, and wherein the wireless receiver is configured to receive the magnetically-coupled energy.

3. The apparatus of claim 2, comprising a transmitter configured to provide the magnetically-coupled energy, and wherein the transmitter is sized and shaped to be located subcutaneously within a patient, or outside a patient body.

4. The apparatus of claim 1, wherein the electrostimulation circuit is configured to deliver an electrostimulation including enough of the received wireless energy to depolarize cardiac tissue near the wireless electrostimulation electrode assembly.

5. The apparatus of claim 1, wherein the first expandable support includes a shape memory material configured to provide an expansion force, and the first expandable support is configured to anchor the first wireless electrostimulation electrode assembly at the implant location at the annulus of the mitral valve at least in part using the expansion force when the first wireless electrostimulation electrode assembly is delivered to the implant location.

6. The apparatus of claim 1, wherein the first wireless electrostimulation electrode assembly includes one or more extending tines configured to controllably extend into tissue when the first wireless electrostimulation electrode assembly is delivered to the implant location at the annulus of the mitral valve of the heart.

7. The apparatus of claim 1, comprising:
a second wireless electrostimulation electrode assembly configured to be intravascularly delivered to an implant location within a blood vessel and configured to provide an electrostimulation to the heart near the blood vessel; and
a controller communicatively coupled to the first and second wireless electrostimulation electrode assemblies and configured to coordinate delivery of the electrostimulation by the first and second wireless electrostimulation electrode assemblies.

8. The apparatus of claim 7, wherein the blood vessel is selected from a list including a pulmonary vein, a coronary sinus, or a vena cava.

9. The apparatus of claim 1, comprising a second electrostimulation electrode assembly configured to be intravascularly delivered to an endocardial location at an atrial appendage of the heart and configured to provide an electrostimulation to the heart; and
a controller communicatively coupled to the first and second wireless electrostimulation electrode assemblies and configured to coordinate delivery of the electrostimulation by the first and second wireless electrostimulation electrode assemblies.

10. The apparatus of claim 9, wherein the atrial appendage of the heart is a left atrial appendage, and wherein the second electrostimulation electrode assembly includes a second expandable support configured to at least partially block the opening to the left atrial appendage of the heart and configured to anchor the second electrostimulation electrode assembly at the opening of the left atrial appendage when the second expandable support is expanded.

11. The apparatus of claim 1, comprising:
a plurality of separate wireless electrostimulation electrode assemblies, each configured to be intravascularly delivered to a respective implant location and each configured to provide an electrostimulation to the heart at the respective implant location;
a controller communicatively coupled to the plurality of separate wireless electrostimulation electrode assemblies and configured to coordinate delivery of the electrostimulation to the heart at each respective implant location; and
wherein the plurality of separate wireless electrostimulation electrode assemblies includes the first wireless electrostimulation electrode assembly.

12. The apparatus of claim 11, wherein the plurality of separate wireless electrostimulation electrode assemblies includes one or more wireless electrostimulation electrode assemblies selected from a list including:
a second wireless electrostimulation electrode assembly configured to be intravascularly delivered to an endocardial location at an atrial septum of the heart and configured to provide an electrostimulation to the heart;
a third wireless electrostimulation electrode assembly configured to be intravascularly delivered to an endocardial location at an atrial appendage of the heart and configured to provide an electrostimulation to the heart; and
a fourth wireless electrostimulation electrode assembly configured to be intravascularly delivered to an implant location within a pulmonary vein and configured to provide an electrostimulation to the heart;
a fifth wireless electrostimulation electrode assembly configured to be intravascularly delivered to an implant location within a vena cava and configured to provide an electrostimulation to the heart;
a sixth wireless electrostimulation electrode assembly configured to be intravascularly delivered to an implant location within a coronary sinus and configured to provide an electrostimulation to the heart;
wherein the controller is communicatively coupled to each corresponding wireless electrostimulation electrode assembly and the controller is configured to coordinate delivery of the electrostimulation to the heart at each respective implant location by each respective wireless electrostimulation electrode assembly.

13. The apparatus of claim 11, wherein the controller includes an arrhythmia detector configured to detect an arrhythmia, and wherein the controller is configured to coordinate delivery of the electrostimulation to the heart at each respective implant location to terminate the arrhythmia in response to information provided by the arrhythmia detector.

14. The apparatus of claim 13, wherein the arrhythmia includes an atrial tachyarrhythmia selected from a list including an atrial fibrillation, an atrial tachycardia, an atrial flutter, an atrioventricular nodal reentrant tachycardia, or an atrioventricular reentrant tachycardia.

15. The apparatus of claim 13, wherein the controller is configured to coordinate delivery of the electrostimulation to the heart at each respective implant location to terminate the arrhythmia without exceeding a pain threshold of a patient.

16. A method, comprising:
receiving wireless energy using a first wireless electrostimulation electrode assembly;

delivering at least some of the received wireless energy as an electrostimulation to a heart;
mechanically supporting the first wireless electrostimulation electrode assembly at least partially using a ring formed by an annulus of a mitral valve of the heart;
wherein the first wireless electrostimulation electrode assembly is configured to be intravascularly delivered to an implant location within a chamber of the heart at the annulus of the mitral valve of the heart; and
wherein the first wireless electrostimulation electrode assembly is configured to fit entirely within the heart.

17. The method of claim 16, comprising:
receiving wireless energy using a plurality of separate wireless electrostimulation electrode assemblies, the plurality including the first wireless electrostimulation electrode assembly, and wherein the plurality of separate wireless electrostimulation electrode assemblies are each configured to be intravascularly delivered to a respective implant location;
delivering one or more coordinated electrostimulations to the heart at the respective implant location using at least one of the plurality of electrostimulation electrode assemblies and using at least some of the received wireless energy.

18. The method of claim 17, including:
detecting an arrhythmia;
terminating the detected arrhythmia using the delivering one or more coordinated electrostimulations and using information provided by the detecting the arrhythmia; and
wherein the delivering one or more coordinated electrostimulations includes delivering enough received wireless energy to depolarize cardiac tissue at each respective implant location where the one or more coordinated electrostimulations are delivered.

19. The method of claim 18, wherein the detecting the arrhythmia includes detecting an atrial arrhythmia selected from a list including an atrial fibrillation, an atrial tachycardia, an atrial flutter, an atrioventricular nodal reentrant tachycardia, or an atrioventricular reentrant tachycardia.

20. The method of claim 18, wherein the terminating the arrhythmia using the delivering one or more coordinated electrostimulations includes depolarizing enough cardiac tissue to terminate the arrhythmia without exceeding a pain threshold of a patient.

* * * * *